United States Patent
Surviladze et al.

(10) Patent No.: US 11,045,519 B2
(45) Date of Patent: Jun. 29, 2021

(54) ARGININE-RICH POLYPEPTIDE COMPOSITIONS AND METHODS OF USING SAME

(71) Applicant: UNM Rainforest Innovations, Albuquerque, NM (US)

(72) Inventors: Zurab Surviladze, Albuquerque, NM (US); Michelle A. Ozbun, Albuquerque, NM (US); Andrew Cowan, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 16/482,009

(22) PCT Filed: Jan. 31, 2018

(86) PCT No.: PCT/US2018/016151
§ 371 (c)(1),
(2) Date: Jul. 30, 2019

(87) PCT Pub. No.: WO2018/144545
PCT Pub. Date: Aug. 9, 2018

(65) Prior Publication Data
US 2019/0351013 A1    Nov. 21, 2019

Related U.S. Application Data

(60) Provisional application No. 62/532,421, filed on Jul. 14, 2017, provisional application No. 62/452,524, filed on Jan. 31, 2017.

(51) Int. Cl.
| | | |
|---|---|---|
| *A61K 38/00* | (2006.01) | |
| *A61K 38/08* | (2019.01) | |
| *A61K 38/10* | (2006.01) | |
| *A61K 38/16* | (2006.01) | |
| *A61K 47/36* | (2006.01) | |
| *A61P 31/20* | (2006.01) | |
| *A61K 9/00* | (2006.01) | |

(52) U.S. Cl.
CPC ............ *A61K 38/16* (2013.01); *A61K 9/0014* (2013.01); *A61K 9/0034* (2013.01); *A61K 38/08* (2013.01); *A61K 38/10* (2013.01); *A61K 38/162* (2013.01); *A61K 47/36* (2013.01)

(58) Field of Classification Search
CPC ........ A61K 38/00; A61K 38/08; A61K 38/10; A61K 38/16; A61K 38/162; A61K 47/36; A61K 9/0014; A61K 9/0034; A61K 9/145; A61P 31/20
See application file for complete search history.

(56) References Cited

U.S. PATENT DOCUMENTS

| | | | |
|---|---|---|---|
| 6,686,333 B1 | 2/2004 | Kashanchi et al. | |
| 8,088,888 B2 | 1/2012 | O'Neil | |
| 8,389,706 B2 | 3/2013 | Weiner et al. | |
| 2005/0171053 A1 | 8/2005 | Blakemore et al. | |
| 2008/0044386 A1* | 2/2008 | Ji ................... | A61K 48/0041 424/93.2 |
| 2010/0189730 A1 | 7/2010 | Weiner et al. | |
| 2011/0086044 A1 | 4/2011 | Kast | |
| 2017/0014459 A1* | 1/2017 | Losa Dominguez ... | A61P 15/00 |

FOREIGN PATENT DOCUMENTS

| | | |
|---|---|---|
| EA | 023892 B1 | 7/2016 |
| EP | 2 178 533 B1 | 3/2013 |
| WO | WO 2006/084131 A2 | 8/2006 |
| WO | WO 2011/145056 A1 | 11/2011 |

OTHER PUBLICATIONS

Yusuf M., "Natural Antimicrobial Agents for Food Biopreservation," ScienceDirect, pp. 1-8. (Year: 2018).*
Gonzalez-Aramundiz et al., "Protamine-based nanoparticles as new antigen delivery systems," European Journal of Pharmaceutics and Biopharmaceutics, 2015, 9&; 51-59. (Year: 2015).*
He et al., "Low molecular weight protamine (LMWP): A nontoxic protamine substitute and an effective cell-penetrating peptide," Journal of Controlled Release, 2014, 193: 63-71. (Year: 2014).*
Cunha et al., "Characterization of Commercially Available Vaginal Lubricants: A Safety Perspective," Pharmaceutics, 2014, 6: 530-542. (Year: 2014).*
Wang et al, "Degradable Hyaluronic Acid/Protamine Sulfate Interpolyelectrolyte Complexes as miRNA-Delivery Nanocapsules for Triple-Negative Breast Cancer Therapy," Advanced Healthcare Materials, 2015, 4: 281-290. (Year: 2015).*

(Continued)

*Primary Examiner* — Julie Ha
(74) *Attorney, Agent, or Firm* — Mueting Raasch Group

(57) ABSTRACT

An arginine-rich polypeptide composition includes an arginine-rich polypeptide and a pharmaceutically acceptable carrier. Generally, the arginine-rich polypeptide has at least nine arginine residues that represent at least 10% of the amino acid residues in the polypeptide. The arginine-rich polypeptide may be used in a method of inhibiting a human papilloma virus (HPV) from binding to a cell, a method of inhibiting intracellular processing of human papilloma virus (HPV) by a cell, or a method of treating a subject having, or at risk of having, a human papilloma virus (HPV) infection.

23 Claims, 20 Drawing Sheets
Specification includes a Sequence Listing.

(56) References Cited

OTHER PUBLICATIONS

International Patent Application No. PCT/US2018/016151 filed Jan. 31, 2018, International Preliminary Report on Patentability dated Aug. 15, 2019, 6 pages.
International Patent Application No. PCT/US2018/016151 filed Jan. 31, 2018, International Search Report and Written Opinion dated Jun. 14, 2018, 5 pages.
Ahmadi et al., Antiviral Potential of Algae Polysaccharides Isolated from Marine Sources: A Review. *Biomed Res Int* 2015, 825203 (2015).
Bae et al., Intelligent polymeric micelles from functional poly(ethylene glycol)-poly(amino acid) block copolymers. *Advanced drug delivery reviews* 61, 768-784, (2009).
Brogden, Antimicrobial peptides: pore formers or metabolic inhibitors in bacteria? *Nature reviews. Microbiology* 3, 238-250, (2005).
Buck et al., Carrageenan is a potent inhibitor of papillomavirus infection. *PLoS Pathog* 2, e69 (2006).
Buck et al. Human alpha-defensins block papillomavirus infection. *Proceedings of the National Academy of Sciences of the United States of America* 103, 1516-1521, (2006).
Cameron et al., Polyarginines are potent furin inhibitors. *The Journal of biological chemistry* 275, 36741-36749, (2000).
Campo, Animal models of papillomavirus pathogenesis. *Virus research* 89, 249-261 (2002).
Campos et al., Two highly conserved cysteine residues in HPV16 L2 form an intramolecular disulfide bond and are critical for infectivity in human keratinocytes. *PLoS One* 4, e4463 (2009).
Centers for Disease Control and Prevention, "Trends in Reportable Sexually Transmitted Diseases in the United States, 2006: National Surveillance Data for Chlamydia, Gonorrhea, and Syphilis", Centers for Disease Control and Prevention, National Center for HIV Viral Hepatitis STD and TB Prevention, Publication ID: 35513, Published Nov. 1, 2007. Content available online at <https://www.thebodypro.com/article/trends-reportable-sexually-transmitted-diseases-united-states-200>. Retrieved from the internet on Sep. 9, 2020.
Culp et al., Human papillomaviruses bind a basal extracellular matrix component secreted by keratinocytes which is distinct from a membrane-associated receptor. *Virology* 347, 147-159 (2006).
Day et al., Identification of a role for the trans-Golgi network in human papillomavirus 16 pseudovirus infection. *Journal of virology* 87, 3862-3870, (2013).
Day et al., Mechanisms of human papillomavirus type 16 neutralization by 12 cross-neutralizing and 11 type-specific antibodies. *Journal of virology* 82, 4638-4646, (2008).
Dugan et al., Human alpha-defensins inhibit BK virus infection by aggregating virions and blocking binding to host cells. *The Journal of biological chemistry* 283, 31125-31132, (2008).
Esko et al., Animal cell mutants defective in glycosaminoglycan biosynthesis. *Proceedings of the National Academy of Sciences of the United States of America* 82, 3197-3201 (1985).
Gillison et al., Chapter 9: Role of mucosal human papillomavirus in nongenital cancers. *J Natl Cancer Inst Monogr*, 57-65 (2003).
Giroglou et al., Human papillomavirus infection requires cell surface heparan sulfate. *J Virol* 75, 1565-1570 (2001).
Gonzalez-Aramundiz et al., Polypeptides and polyaminoacids in drug delivery. *Expert opinion on drug delivery* 9, 183-201, (2012).
Gounder et al., Critical determinants of human alpha-defensin 5 activity against non-enveloped viruses. *The Journal of biological chemistry* 287, 24554-24562, (2012).
Hess et al., Cellular binding, motion, and internalization of synthetic gene delivery polymers. *Biochimica et biophysica acta* 1773, 1583-1588, (2007).
Joyce et al., The L1 major capsid protein of human papillomavirus type 11 recombinant virus-like particles interacts with heparin and cell-surface on human keratinocytes. *The Journal of biological chemistry* 274, 5810-5822 (1999).
Kacprzak et al. Inhibition of furin by polyarginine-containing peptides: nanomolar inhibition by nona-D-arginine. *The Journal of biological chemistry* 279, 36788-36794, (2004).

Kibler et al., Polyarginine inhibits gp160 processing by furin and suppresses productive human immunodeficiency virus type 1 infection. *J Biol Chem* 279, 49055-49063 (2004).
Krebs et al., Sodium dodecyl sulfate and C31G as microbicidal alternatives to nonoxynol 9: comparative sensitivity of primary human vaginal keratinocytes. *Antimicrobial agents and chemotherapy* 44, 1954-1960 (2000).
Lidholt et al., A single mutation affects both N-acetylglucosaminyltransferase and glucuronosyltransferase activities in a Chinese hamster ovary cell mutant defective in heparan sulfate biosynthesis. *Proceedings of the National Academy of Sciences of the United States of America* 89, 2267-2271 (1992).
Mislick et al., Evidence for the role of proteoglycans in cation-mediated gene transfer. *Proceedings of the National Academy of Sciences of the United States of America* 93, 12349-12354 (1996).
Mistry et al., The anti-papillomavirus activity of human and bovine lactoferricin. *Antiviral research* 75, 258-265, (2007).
Monie et al., Cervarix: a vaccine for the prevention of HPV 16, 18-associated cervical cancer. *Biologics: Targets & Therapy* 2, 97-105 (2008).
Niruthisard, S., Roddy, R. E. & Chutivongse, S. The effects of frequent nonoxynol-9 use on the vaginal and cervical mucosa. *Sexually transmitted diseases* 18, 176-179 (1991).
Ozbun, Human papillomavirus type 31b infection of human keratinocytes and the onset of early transcription. *Journal of virology* 76, 11291-11300 (2002).
Ozbun, Infectious human papillomavirus type 31b: purification and infection of an immortalized human keratinocyte cell line. *The Journal of general virology* 83, 2753-2763, (2002).
Ozcelik et al., Harnessing the multifunctionality in nature: a bioactive agent release system with self-antimicrobial and immunomodulatory properties. *Advanced healthcare materials* 4, 2026-2036, (2015).
Paris et al., Opposing roles of syndecan-1 and syndecan-2 in polyethyleneimine-mediated gene delivery. *The Journal of biological chemistry* 283, 7697-7704, (2008).
Pasquato et al., Viral envelope glycoprotein processing by proprotein convertases. *Antiviral research* 99, 49-60, (2013).
Patterson et al., Human papillomavirus type 31b infection of human keratinocytes does not require heparan sulfate. *Journal of virology* 79, 6838-6847, (2005).
Payne et al., Internalization and trafficking of cell surface proteoglycans and proteoglycan-binding ligands. *Traffic* 8, 389-401, (2007).
Ramos-Molina et al., Cationic Cell-Penetrating Peptides Are Potent Furin Inhibitors. *PloS one* 10, e0130417, (2015).
Roberts et al., Genital transmission of HPV in a mouse model is potentiated by nonoxynol-9 and inhibited by carrageenan. *Nature medicine* 13, 857-861, (2007).
Schiffman et al., Chapter 2: Natural history of anogenital human papillomavirus • infection and neoplasia. *J Natl Cancer Inst Monogr*, 14-19 (2003).
Schiller et al., Current understanding of the mechanism of HPV infection. *Gynecologic oncology* 118, S12-17, (2010).
Schiller et al., Delivering on the promise: HPV vaccines and cervical cancer. *Nat Rev Microbiol* 2, 343-347 (2004).
Smith et al., Mechanism of adenovirus neutralization by Human alpha-defensins. *Cell host & microbe* 3, 11-19, (2008).
Surviladze et al., Essential roles for soluble virion-associated heparan sulfonated proteoglycans and growth factors in human papillomavirus infections. *PLoS Pathog* 8, e1002519 (2012).
Tenge et al., Delineation of interfaces on human alpha-defensins critical for human adenovirus and human papillomavirus inhibition. *PLoS pathogens* 10, e1004360, (2014).
Tyler et al., Immunization with a consensus epitope from human papillomavirus L2 induces antibodies that are broadly neutralizing. *Vaccine* 32, 4267-4274, (2014).
Wiens et al., Alpha-defensin HD5 inhibits furin cleavage of human papillomavirus 16 L2 to block infection. *J Virol* 89, 2866-2874 (2015).
Yusef, et al., "Natural Antimicrobial Agents for Food Biopreservation", *Science Direct*, 2018, pp. 1-8.

(56) References Cited

OTHER PUBLICATIONS

Ahmadi et al., Antiviral Potential of Algae Polysaccharides Isolated from Marine Sources: A Review. *BioMed Research International*, 2015, 825203 (2015).
Ali et al., A 3-O-sulfated heparan sulfate binding peptide preferentially targets herpes simplex virus 2-infected cells. *J Virol* 86, 12:6434-6443 (2012).
Almond, Hyaluronan. *Cell Mol Life Sci* 64, 1591-1596 (2007).
Ando et al., Protamines. Isolation, characterization, structure and function. *Mol Biol Biochem Biophys* 12, 1-114 (1973).
Aquino et al., Diverse functions of glycosaminoglycans in infectious diseases. *Prog Mol Biol Transl Sci* 93, 373-394 (2010).
Aspedon et al., The antibacterial action of protamine: evidence for disruption of cytoplasmic membrane energization in *Salmonella typhimurium*. *Microbiology (Reading)* 142 ( Pt 12), 3389-3397 (1996).
Aya et al., Hyaluronan in wound healing: rediscovering a major player. *Wound Repair Regen* 22, 579-593 (2014).
Bartlett et al., Proteoglycans in host-pathogen interactions: molecular mechanisms and therapeutic implications. *Expert Rev Mot Med* 12, e5 (2010).
Bekemeier et al., Carrageenin-induced thrombosis in rats and mice: a model for testing antithrombotic substances? *Agents Actions* 16, 5:446-451 (1985).
Bhattacharyya et al., Carrageenan induces cell cycle arrest in human intestinal epithelial cells in vitro. *J Nutr* 138, 469-475 (2008).
Bhattacharyya et al., Carrageenan Inhibits Insulin Signaling through GRB10-mediated Decrease in Tyr(P)-IRS1 and through Inflammation-induced Increase in Ser(P)307-IRS1. *J Biol Chem* 290, 10764-10774 (2015).
Bhattacharyya et al., Toll-like receptor 4 mediates induction of the Bcl10-NFkappaB-interleukin-8 inflammatory pathway by carrageenan in human intestinal epithelial cells. *J Biol Chem* 283, 10550-10558 (2008).
Bhattacharyya et al., Carrageenan-induced colonic inflammation is reduced in Bcl10 null mice and increased in IL-10-deficient mice. *Mediators Inflamm* 2013, 397642 (2013).
Borthakur et al., Carrageenan induces interleukin-8 production through distinct Bcl10 pathway in normal human colonic epithelial cells. *Am J Physiol Gastrointest Liver Physiol* 292, G829-838 (2007).
Boyer et al., E7 protein of human papilloma virus-16 induces degradation of retinoblastoma protein through the ubiquitin-proteasome pathway. *Cancer Res* 56, 4620-4624 (1996).
Buck et al., Carrageenan Is a Potent Inhibitor of Papillomavirus Infection. *PLoS Pathogens*, 2, 7 e69, 0671-0680 (2006).
Campos et al., Two Highly Conserved Cysteine Residues in HPV16 L2 Form an Intramolecular Disulfide Bond and Are Critical for Infectivity in Human Keratinocytes. *PLoS One* 4(2) e4463 (2009).
X Chen et al., Evaluation of the efficacy and safety of hyaluronic acid vaginal gel to ease vaginal dryness: a multicenter, randomized, controlled, open-label, parallel-group, clinical trial. *J Sex Med* 10, 1575-1584 (2013).
Chen et al., Microbial subversion of heparan sulfate proteoglycans. *Mol Cells* 26, 415-426 (2008).
Clement et al., A novel role for phagocytosis-like uptake in herpes simplex virus entry. *J Cell Biol* 174, 1009-1021 (2006).
Cohen et al., A critical review of the toxicological effects of carrageenan and processed eucheuma seaweed on the gastrointestinal tract. *Crit Rev Toxicol* 32(5), 413-444 (2002).
Damania, DNA tumor viruses and human cancer. *TRENDS in Microbiology* 15(1) 38-44 (2006).
De Francesco et al., HIV-1 p17 matrix protein interacts with heparan sulfate side chain of CD44v3, syndecan-2, and syndecan-4 proteoglycans expressed on human activated CD4+ T cells affecting tumor necrosis factor alpha and interleukin 2 production. *J Biol Chem* 286, 19541-19548 (2011).

Ekin et al., The comparison of hyaluronic acid vaginal tablets with estradiol vaginal tablets in the treatment of atrophic vaginitis: a randomized controlled trial. *Arch Gynecol Obstet* 283, 539-543 (2011).
Gallay, Syndecans and HIV-1 pathogenesis. *Microbes Infect* 6, 617-622 (2004).
Gardner et al., Heparan sulfate binding by natural eastern equine encephalitis viruses promotes neurovirulence. *Proc Natl Acad Sci U S A* 108, 16026-16031 (2011).
Gillison et al., Chapter 9: Role of Mucosal Human Papillomavirus in Nongenital Cancers. *J. Natl. Cancer Inst. Monogr.* 31:57-65 (2003).
Gonzalez et al., Polysaccharides as antiviral agents: antiviral activity of carrageenan. *Antimicrob Agents Chemother* 31, 9:1388-1393 (1987).
Grimaldi et al., Role of high molecular weight hyaluronic acid in postmenopausal vaginal discomfort. *Minerva Ginecol* 64, 321-329 (2012).
Hansen et al., Solubility and antimicrobial efficacy of protamine on *Listeria monocytogenes* and *Escherichia coli* as influenced by pH. *J Appl Microbiol* 88, 1049-1055 (2000).
Hellner et al., HPV16 E7 oncogene expression in normal human epithelial cells. causes molecular changes indicative of an epithelial to mesenchymal transition. *Virology* 391, 57-63 (2009).
Imamura et al., Single particle tracking confirms that multivalent Tat protein transduction domain-induced heparan sulfate proteoglycan cross-linkage activates Rac1 for internalization. *J Biol Chem* 286, 10581-10592 (2011).
Ishioka et al., Induction of colorectal tumors in rats by sulfated polysaccharides. *Crit Rev Toxicol* 17, 215-244 (1987).
Jaques, Protamine—antagonist to heparin. *Can Med Assoc J* 108, 1291-1297 (1973).
Jiang et al., kappa-carrageenan induces the disruption of intestinal epithelial Caco-2 monolayers by promoting the interaction between intestinal epithelial cells and immune cells. *Mol Med Rep* 8, 1635-1642 (2013).
Johansen et al., Protamine-induced permeabilization of cell envelopes of gram-positive and gram-negative bacteria. *Appl Environ Microbiol* 63(3), 1155-1159 (1997).
Johnson et al., Role of heparan sulfate in attachment to and infection of the murine female genital tract by human papillomavirus. *J Virol* 83(5), 2067-2074 (2009).
Jones et al., Analysis of the p53-mediated G1 growth arrest pathway in cells expressing the human papillomavirus type 16 E7 oncoprotein. *J Virol* 71, 2905-2912 (1997).
Juraskova et al., The acceptability, feasibility, and efficacy (phase I/II study) of the OVERcome (Olive Oil, Vaginal Exercise, and MoisturizeR) intervention to improve dyspareunia and alleviate sexual problems in women with breast cancer. *J Sex Med* 10, 2549-2558 (2013).
Karasneh et al., An important role for syndecan-1 in herpes simplex virus type-1 induced cell-to-cell fusion and virus spread. *PLoS One* 6, e25252 (2011).
Katz et al., Hemodynamics of protamine administration. Comparison of right atrial, left atrial, and aortic injections. *J Thorac Cardiovasc Surg* 94, 881-886 (1987).
Kerur et al., Characterization of entry and infection of monocytic THP-1 cells by Kaposi's sarcoma associated herpesvirus (KSHV): role of heparan sulfate, DC-SIGN, integrins and signaling. *Virology* 406, 103-116 (2010).
Kibler et al., Polyarginine Inhibits gp160 Processign by Furin and Suppresses Productive Human Immunodeficiency Virus Type 1 Infection. *J. of Bio. Chem.* 279(47) 49055-49063 (2004).
Lee et al., Hyaluronan: a multifunctional, megaDalton, stealth molecule. *Curr Opin Cell Biol* 12, 581-586 (2000).
Litwiniuk et al., Hyaluronic Acid in Inflammation and Tissue Regeneration. *Wounds* 28, 78-88 (2016).
Moelleken et al., The Chlamydia outer membrane protein OmcB is required for adhesion and exhibits biovar-specific differences in glycosaminoglycan binding. *Mol Microbiol* 67, 403-419 (2008).
Munoz et al., Risk factors for HPV DNA detection in middle-aged women. *Sex Transm Dis* 23, 504-510 (1996).

(56) References Cited

OTHER PUBLICATIONS

Nachtigall, Comparative study: Replens versus local estrogen in menopausal women. *Fertil Steril* 61, 178-180 (1994).
Nyberg et al., The low molecular weight heparan sulfate-mimetic, PI-88, inhibits cell-to-cell spread of herpes simplex virus. *Antiviral Res* 63, 15-24 (2004).
O'Hanlon et al., Vaginal pH measured in vivo: lactobacilli determine pH and lactic acid concentration. *BMC Microbiol* 19, 13 (2019).
Oh et al., A role for heparan sulfate in viral surfing. *Biochem Biophys Res Commun* 391, 176-181 (2010).
Owens, Insulin preparations with prolonged effect. *Diabetes Technol Ther* 13 Suppl 1, S5-14 (2011).
Ozbun et al., " Protamine Sulfate Is a Potent Inhibitor of Human Papillomavirus Infections Via Targeting Virion Attachment to Heparan Sulfonated Proteoglycans," International Papillomavirus Conference IPVC 2018, (International Papillomavirus Society) Sydney Australia, Oct. 2, 2018-Oct. 6, 2018.
Porsche et al., Allergy to protamine sulfate. *Heart Lung* 28, 418-428 (1999).
Potter et al., Inhibition of foodborne bacteria by native and modified protamine: • importance of electrostatic interactions. *Int J Food Microbiol* 103, 23-34 (2005).
Prevo et al., Mouse LYVE-1 is an endocytic receptor for hyaluronan in lymphatic endothelium. *J Biol Chem* 276, 19420-19430 (2001).
Rudolf, [New form of insulin: crystallized protamine insulin (NPH 50)]. *Concours Med* 73, 3755-3757 (1951).
Sapp et al., Viral entry mechanisms: human papillomavirus and a long journey from extracellular matrix to the nucleus. *FEBS J* 276, 7206-7216 (2009).
Satoh et al., Effects of intrathecal antibodies to substance P, calcitonin gene-related peptide and galanin on repeated cold stress-induced hyperalgesia: comparison with carrageenan-induced hyperalgesia. *Pain* 49, 273-278 (1992).
Schiller et al., Delivering on the promise: HPV vaccines and cervical cancer. *Nature Reviews: Microbiology* 2:343-347 (2004).
Schulze et al., Hepatitis B virus infection initiates with a large surface protein-dependent binding to heparan sulfate proteoglycans. *Hepatology* 46, 1759-1768 (2007).
Selinka et al., Inhibition of transfer to secondary receptors by heparan sulfate-binding drug or antibody induces noninfectious uptake of human papillomavirus. *J Virol* 81, 10970-10980 (2007).
Selinka et al., Further evidence that papillomavirus capsids exist in two distinct conformations. *J Virol* 77, 12961-12967 (2003).
Shukla et al., Herpesviruses and heparan sulfate: an intimate relationship in aid of viral entry. *J Clin Invest* 108, 503-510 (2001).
Smith et al., Persistent HPV infection in postmenopausal age women. *Int J Gynaecol Obstet* 87, 131-137 (2004).
Smith et al., Prevalence and persistence of human papillomavirus in postmenopausal age women. *Cancer Detect Prev* 27, 472-480 (2003).
Stute, Is vaginal hyaluronic acid as effective as vaginal estriol for vaginal dryness relief? *Arch Gynecol Obstet* 288, 1199-1201 (2013).
Surviladze et al., Essential Roles for Soluble Virion-Associated Heparan Sulfonated Proteoglycans and Growth Factors in Human Papillomavirus Infections. *PLos Pathogens*, 8(2) e1002519 (2012).
Suzuki et al., Studies on protamines. XVII. The complete amino acid sequence of clupeine YI. *J Biochem* 72, 1433-1446 (1972).
Tamura et al., Genogroup II noroviruses efficiently bind to heparan sulfate proteoglycan associated with the cellular membrane. *J Virol* 78(8), 3817-3826 (2004).

Teng et al., Molecular functions of syndecan-1 in disease. *Matrix Biol* 31, 3-16 (2012).
Tiwari et al., Anti-heparan sulfate peptides that block herpes simplex virus infection in vivo. *J Biol Chem* 286, 25406-25415 (2011).
Tiwari et al., Role of heparan sulfate in sexually transmitted infections. *Glycobiology* 22, 1402-1412 (2012).
Tobacman, Review of harmful gastrointestinal effects of carrageenan in animal experiments. *Environ Health Perspect* 109, 983-994 (2001).
Tobacman et al., The carrageenan diet: not recommended. *Science* 321, 1040-1041 (2008).
Wadstrom et al., Glycosaminoglycan-binding microbial proteins in tissue adhesion and invasion: key events in microbial pathogenicity. *J Med Microbiol* 48, 223-233 (1999).
Weiler et al., Serious adverse reactions to protamine sulfate: are alternatives needed? *J Allergy Clin Immunol* 75, 297-303 (1985).
Weinstock et al., Sexually transmitted diseases among American youth: incidence and prevalence estimates, 2000. *Perspect Sex Reprod Health* 36, 6-10 (2004).
Welsby et al., Hemodynamic changes after protamine administration: association with mortality after coronary artery bypass surgery. *Anesthesiology* 102, 308-314 (2005).
Wiens et al., Alpha-Defensin HD5 Inhibits Furin Cleavage of Human Papillomavirus 16 L2 to Block Infection. *J. Virology* 89(5) 2866-2874 (2015).
Yamamoto et al., Inhibition of herpes virus adsorption on cells by protamine. *Kurume Med J* 16, 83-89 (1969).
Young et al., "Protamine Sulfate Potently Reduces HPV Infection by Preventing Attachment to Heparan Sulfate Proteoglycans." EUROGIN, Abstract No. 566, FC 25—Viral and Molecular Biology (International Multidisciplinary HPV Congress) Monaco, Dec. 4, 2019-Dec. 7, 2019.
Young et al., "Protamine Sulfate Reduces HPV Infection by Preventing Attachment to Heparan Sulfate Proteoglycans," The Arturo Falaschi Conference series 2019 "ICGEB DNA Tumour Virus Meeting—50th Anniversary" (International Centre for Genetic Engineering and Biotechnology) Trieste, Italy, Jul. 9, 2019-Jul. 14, 2019.
Young et al., "Viral Entry: An Opportunity to Understand and Prevent Human Papillomavirus Infections," Molecular Biology of DNA Tumor Viruses Conference, Madison Wisconsin, Jul. 31, 2018-Aug. 4, 2018.
Biziagos et al., Effect of antiviral substances on hepatitis a virus replication in vitro. *J Med Virol* 22, 57-66 (1987).
Ceballos et al., Spermatozoa capture HIV-1 through heparan sulfate and efficiently transmit the virus to dendritic cells. *J Exp Med* 206, 2717-2733 (2009).
Ferenczy et al., Human papillomavirus infection in postmenopausal women with and without hormone therapy. *Obstet Gynecol* 90, 7-11 (1997).
McLaughlin-Drubin et al., The human papillomavirus E7 oncoprotein. *Virology* 384, 335-344 (2009).
Merilahti et al., Role of Heparan Sulfate in Cellular Infection of Integrin-Binding Coxsackievirus A9 and Human Parechovirus 1 Isolates. *PLoS One* 11, e0147168 (2016).
Munger et al., Mechanisms of human papillomavirus-induced oncogenesis. *J Virol* 78, 11451-11460 (2004).
Rodman et al., Protamine-DNA association in mammalian spermatozoa. *Exp Cell Res* 150, 269-281 (1984).
Tamivii et al., Hyaluronan and homeostasis: a balancing act. *J Biol Chem* 277, 4581-4584 (2002).
Tatiana et al., BLAST 2 Sequences, a new tool for comparing protein and nucleotide sequences, *FEMS Mierobiol Lett*, 174, 247-250 (1999).

\* cited by examiner (A)

(B)

(A)

(B)

(A)

(B)

(A)

(B)

(A)

(B)

(C)

(A)

(B)

(A)

(B)

(A)

(B)

(A)

(B)

(A)

(B)

SEQUENCE LISTING

<160> NUMBER OF SEQ ID NOS: 13

<210> SEQ ID NO 1
<211> LENGTH: 20
<212> TYPE: PRT
<213> ORGANISM: Artificial Sequence
<220> FEATURE:
<223> OTHER INFORMATION: Polypeptide

<400> SEQUENCE: 1

Tyr Gly Arg Lys Lys Arg Arg Gln Arg Arg Cys Ser Thr Arg Ile
1               5                   10                  15

Arg Arg Gln Leu
            20

<210> SEQ ID NO 2
<211> LENGTH: 18
<212> TYPE: PRT
<213> ORGANISM: Artificial Sequence
<220> FEATURE:
<223> OTHER INFORMATION: Polypeptide

<400> SEQUENCE: 2

Arg Lys Lys Arg Arg Gln Arg Arg Cys Leu Arg Ile Thr Arg Gln
1               5                   10                  15

Ser Arg

<210> SEQ ID NO 3
<211> LENGTH: 9
<212> TYPE: PRT
<213> ORGANISM: Artificial Sequence
<220> FEATURE:
<223> OTHER INFORMATION: Polypeptide

<400> SEQUENCE: 3

Arg Arg Arg Arg Arg Arg Arg Arg Arg
1               5

<210> SEQ ID NO 4
<211> LENGTH: 11
<212> TYPE: PRT
<213> ORGANISM: Artificial Sequence
<220> FEATURE:
<223> OTHER INFORMATION: Polypeptide

<400> SEQUENCE: 4

Tyr Gly Arg Lys Lys Arg Arg Gln Arg Arg Arg
1               5                   10

<210> SEQ ID NO 5
<211> LENGTH: 28
<212> TYPE: PRT
<213> ORGANISM: Artificial Sequence
<220> FEATURE:
<223> OTHER INFORMATION: Polypeptide

```
<220> FEATURE:
<221> NAME/KEY: REPEAT
<222> LOCATION: (28)..(28)
<223> OTHER INFORMATION: n=1-59

<400> SEQUENCE: 5

Arg Arg Arg Arg Arg Arg Arg Arg Arg Arg Arg Arg Arg Arg Arg
1               5                   10                  15

Arg Arg Arg Arg Arg Arg Arg Arg Arg Arg Arg
            20                  25

<210> SEQ ID NO 6
<211> LENGTH: 51
<212> TYPE: PRT
<213> ORGANISM: Homo Sapiens

<400> SEQUENCE: 6

Met Ala Arg Tyr Arg Cys Cys Arg Ser Gln Ser Arg Ser Tyr Tyr
1               5                   10                  15

Arg Gln Arg Gln Arg Ser Arg Arg Arg Arg Arg Ser Cys Gln Thr
            20                  25                  30

Arg Arg Arg Ala Met Arg Cys Cys Arg Pro Tyr Arg Pro Arg Cys
        35                  40                  45

Arg Arg His
    50

<210> SEQ ID NO 7
<211> LENGTH: 102
<212> TYPE: PRT
<213> ORGANISM: Homo Sapiens

<400> SEQUENCE: 7

Met Val Arg Tyr Arg Val Arg Ser Leu Ser Glu Arg Ser His Glu Val
1               5                   10                  15

Tyr Arg Gln Gln Leu His Gly Gln Glu Gln Gly His His Gly Gln Glu
            20                  25                  30

Glu Gln Gly Leu Ser Pro Glu His Val Glu Val Tyr Glu Arg Thr His
        35                  40                  45

Gly Gln Ser His Tyr Arg Arg His Cys Ser Arg Arg Arg Leu His
    50                  55                  60

Arg Ile His Arg Arg Gln His Arg Ser Cys Arg Arg Lys Arg Arg
65                  70                  75                  80

Ser Cys Arg His Arg Arg Arg His Arg Arg Gly Cys Arg Thr Arg Lys
                85                  90                  95

Arg Thr Cys Arg Arg His
            100

<210> SEQ ID NO 8
<211> LENGTH: 31
<212> TYPE: PRT
<213> ORGANISM: Scylliorhinus caniculus

<400> SEQUENCE: 8

Ala Arg Ser Arg Ser Arg Arg Ser Tyr Gly Arg Gly Arg Arg Gly
1               5                   10                  15

Gly Arg Arg Arg Arg Arg Arg Arg Arg Arg Gly Gly Arg
            20                  25                  30

<210> SEQ ID NO 9
<211> LENGTH: 33
```

```
<212> TYPE: PRT
<213> ORGANISM: Oncorhynchus keta

<400> SEQUENCE: 9

Met Pro Arg Arg Arg Ser Ser Arg Pro Val Arg Arg Arg
1               5                   10                  15

Arg Pro Arg Val Ser Arg Arg Arg Arg Gly Gly Arg Arg Arg
            20                  25                  30

Arg

<210> SEQ ID NO 10
<211> LENGTH: 50
<212> TYPE: PRT
<213> ORGANISM: Bos taurus

<400> SEQUENCE: 10

Ala Arg Tyr Arg Cys Cys Leu Thr His Ser Gly Ser Arg Cys Arg Arg
1               5                   10                  15

Arg Arg Arg Arg Arg Cys Arg Arg Arg Arg Arg Phe Gly Arg Arg
            20                  25                  30

Arg Arg Arg Arg Val Cys Cys Arg Arg Tyr Thr Val Ile Arg Cys Thr
        35                  40                  45

Arg Gln
    50

<210> SEQ ID NO 11
<211> LENGTH: 33
<212> TYPE: PRT
<213> ORGANISM: Oncorhynchus mykiss

<400> SEQUENCE: 11

Pro Arg Arg Arg Arg Arg Ser Ser Ser Arg Pro Ile Arg Arg Arg
1               5                   10                  15

Arg Pro Arg Val Ser Arg Arg Arg Arg Gly Gly Arg Arg Arg
            20                  25                  30

Arg

<210> SEQ ID NO 12
<211> LENGTH: 33
<212> TYPE: PRT
<213> ORGANISM: Oncorhynchus mykiss

<400> SEQUENCE: 12

Met Pro Arg Arg Arg Arg Ser Ser Arg Pro Val Arg Arg Arg
1               5                   10                  15

Arg Pro Arg Val Ser Arg Arg Arg Arg Gly Gly Arg Arg Arg
            20                  25                  30

Arg

<210> SEQ ID NO 13
<211> LENGTH: 31
<212> TYPE: PRT
<213> ORGANISM: Oncorhynchus mykiss

<400> SEQUENCE: 13

Met Pro Arg Arg Arg Ala Ser Arg Ile Arg Arg Arg Arg
1               5                   10                  15

Pro Arg Val Ser Arg Arg Arg Arg Gly Gly Arg Arg Arg Arg
            20                  25                  30
```

ARGININE-RICH POLYPEPTIDE COMPOSITIONS AND METHODS OF USING SAME

CROSS-REFERENCE TO RELATED APPLICATION

This application is the § 371 U.S. National Stage of International Application No. PCT/US2018/016151, filed Jan. 31, 2018, which claims the benefit of U.S. Provisional Patent Application No. 62/452,524, filed Jan. 31, 2017, and U.S. Provisional Patent Application No. 62/532,421, filed Jul. 14, 2017, each of which is incorporated herein by reference.

SEQUENCE LISTING

This application contains a Sequence Listing electronically submitted to the United States Patent and Trademark Office via EFS-Web as an ASCII text file entitled "07-30-2019-SeqList-0310-000120US01.txt" having a size of 8.192 bytes and created on Jul. 30, 2019. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein and does not go beyond the disclosure in the International Application as filed.

GOVERNMENT FUNDING

This invention was made with government support under CA118100 awarded by the National Institutes of Health. The government has certain rights in the invention.

SUMMARY

This disclosure describes compositions that include an arginine-rich polypeptide and methods of treatment that involve administering an arginine-rich polypeptide to a subject. Generally, the composition includes an arginine-rich polypeptide and a pharmaceutically acceptable carrier. Generally, the arginine-rich polypeptide has at least nine arginine residues that represent at least 10% of the amino acid residues in the polypeptide.

In some embodiments, wherein the arginine-rich polypeptide includes protamine. In some of these embodiments, the protamine can be in the form of protamine sulfate (PrS).

In some embodiments, the arginine-rich polypeptide is provided in a complex with hyaluronic acid.

In some embodiments, the arginine-rich polypeptide is provided in a concentration of at least 1 µM.

In some embodiments, the composition is formulated for topical administration.

In another aspect, this disclosure describes a method of inhibiting a human papilloma virus (HPV) from binding to a cell. Generally, the method includes contacting the cell with any embodiment of the composition summarized above in an amount effective to inhibit HPV binding to the cell.

In another aspect, this disclosure describes a method of inhibiting intracellular processing of human papilloma virus (HPV) by a cell. Generally, the method includes contacting the cell with any embodiment of the composition summarized above in an amount effective to inhibit intracellular processing of HPV by the cell.

In another aspect, this disclosure describes a method of treating a subject having, or at risk of having, a human papilloma virus (HPV) infection. Generally, the method includes administering to the subject any embodiment of the composition summarized above in an amount effective to ameliorate at least one symptom or clinical sign of infection of infection by HPV.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
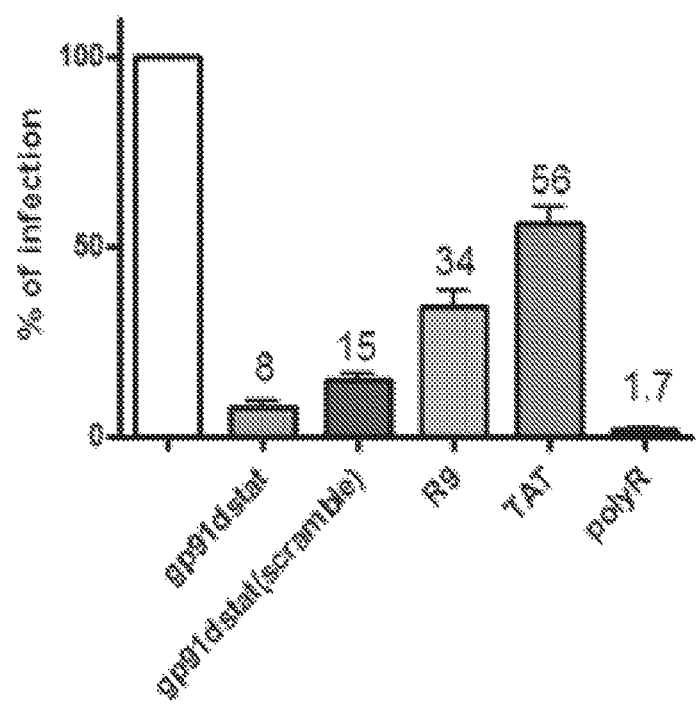
FIG. 1. Arginine-rich peptides efficiently inhibit HPV16 infection. HaCaT cells were cultured in complete growing medium (CM; Dulbecco's modified Eagle's medium nutrient mixture F-12 HAM (Sigma-Aldrich, St. Louis, Mo.)) supplemented with 10% fetal bovine serum (FBS), amino acids (Sigma-Aldrich, St. Louis, Mo.), 2 mM L-glutamine, 100 U/ml penicillin and 1 µg/ml streptomycin (Sigma-Aldrich, St. Louis, Mo.), as previously described (Patterson et al., 2005. *J Virol* 79:6838-6847). Semi-confluent cells were pretreated for 30 minutes with arginine-rich peptides dissolved in CM (6 µM gp91dstat, gp91dstat (scramble), R9, and TAT, or 3 polyR) before the exposure to HaCaT cells and 300 vge/cell HPV16 pseudovirions (PsVs) packaging a luciferase reporter plasmid. Infectivity was scored after 24 hours of incubation at 37° C. (i.e., post infection) by Lumat LB9501 (Berthold Technologies GmbH & Co KG, Bad Wildbad, Germany) equipment, using the luciferase assay kit (Promega, Madison, Wis.) according to manufacturer's specification. Raw data were normalized to total cellular protein concentration. Graph summarizes triplicate treatments; error bars represent SEM.

This disclosure relates to compositions and methods for treating human papilloma virus (HPV) infection. Arginine-rich polypeptides efficiently inhibit HPV activity. Thus, arginine-rich polypeptides can be used to inhibit HPV from binding to a cell, inhibit intracellular processing of HPV by a cell, and/or treat a subject having, or at risk of having, an HPV infection. This disclosure also describes compositions that include an amount of an arginine-rich polypeptide—either alone or complexed with an anionic compound—effective to inhibit infection. For example, the arginine-rich polypeptide may be added to conventional vaginal moisturizers to provide microbicidal activity, particularly anti-HPV activity.

Human papillomaviruses (HPV) are members of the Papillomaviridae family of DNA viruses. HPV infection is a common sexually transmitted infection (STI) that affects both men and women. It is passed from one person to another by skin-to-skin contact, including sexual contact.

There are more than 120 different HPV strains (genotypes) that can affect different parts of the body, including 40 HPV strains that are sexually transmitted and infect the genitals, mouth, and/or throat. The different HPV types are classified into low risk and high risk, based on their association with cancer. "Low risk" types (e.g., types 6 and 11) rarely cause cancer, but can induce benign or low-grade cervical cell changes and genital warts. "High risk" types (e.g., types 16, 18, 31, and 45) have a greater likelihood of causing low-grade and high-grade cervical cell abnormalities that are precursors to cancer and cervical cancer. Infection with high risk types of HPV does not necessarily lead to cancer, but it could be involved in development of vulvar, vaginal, penile, anal and oropharyngeal (i.e., a subset of head-and-neck) cancers. HPV types 16 and 18 are estimated to be involved in 70% of cervical cancer cases, 55% of vaginal cancers, 79% of anal cancers, and 62% of oropharyngeal cancers.

Existing prophylactic HPV vaccines (GARDASIL, Merck & Co., Inc., Kenilworth, N.J.) and CERVARIX, GlaxoSmithKline, plc, Isleworth, London, U.K.) currently licensed in the United States for protection against the most common cancer-associated HPV types protect only against a minor fraction (types HPV-6 and HPV-11 and/or HPV-16 and HPV-18) of the over 120 serotypes, whereas GARDASIL9 protects against an additional five oncogenic HPV types. Therefore, vaccinated males and females may be infected with other types of cancer-associated HPVs, and numerous people worldwide remain unvaccinated for diverse reasons. Thus, there is a need for the development of broad-spectrum antiviral compounds that might be used as topical microbicides that can inhibit transmission of HPVs.

The HPV capsid is positively charged, and therefore binds to a negatively charged heparan sulfate (HS) chain of heparan sulfate proteoglycans (HSPG) on the host cell surface. Although interaction with HS can be viewed as nonspecific, it is well recognized that HS functions as an attachment receptor for HPV. Certain strong anionic or cationic substances have been used to inhibit HPV infection, including several inhibitors described in, for example, WO 2006084131 A2, WO 2011145056 A1, US 2011/0086044, EP 2178533 B1, and US 2005/0171053 A1. Polyanionic molecules could compete with HS for binding to HPV and inhibit virus interaction with an attachment factor. Widely used anionic inhibitors are sulfated polysaccharides obtained from the red algae—e.g., carrageenans, as described in EP 2178533 B1, US 2005/0171053 A1. Different forms of carrageenans are inhibitors of various viral infections, including HPV. Carrageenan resembles HS and, since the affinity of HPV to carrageenan is several orders of magnitude higher that HS, it blocks initial attachment of virus to cells. Additionally, carrageenan exerts a post-attachment inhibitory effect on HPV infectivity.

Alternatively, infection could be inhibited by blocking virus binding sites on the cell membrane. HS is negatively charged and readily binds to positively charged substances. Therefore, cationic substances targeting HS on the surface of the host cell provide an attractive approach for the development of antimicrobial agents. Such targeting of cell surface receptors is a characteristic of short antimicrobial peptides (AMPs). These cationic peptides, secreted by numerous organisms, are characterized by low cytotoxicity and broad spectrum of antimicrobial activity. Cationic peptides rapidly bind to negatively charged HS chains, inducing clustering and internalization of HSPGs. Typically, such internalization is very fast (e.g., minutes) and results in reduced expression of HSPGs on the cell surface. Thus, it is conceivable that polycationic compounds could inhibit HPV binding to target cells via two mechanisms. One mechanism is mediated by blocking primary viral attachment sites on the cell surface. A second mechanism could be induced by rapid internalization and therefore depletion of HSPGs attachment factors from the cell surface.

Several cationic peptides such as, for example, lactoferricin, protamine, and alpha-defensins have shown antiviral activity against various types of HPV. Indeed, HPV inhibitors described in, for example, WO 2006084131 A2 and WO 2011145056 A1 are cationic in nature.

Inhibition of HPV Infection by Arginine-Rich Polypeptides

Arginine-enriched peptides inhibit HPV16 infection. Arginine-rich polypeptides (SEQ ID NO:1-5) were evaluated for their ability to inhibit HPV. SEQ ID NO:1 (gp91 ds-tat) includes a gp91phox sequence linked to the human immunodeficiency virus-tat peptide. The tat sequence facilitates entry of this peptide into the cells. SEQ ID NO:2 (Gp91dstat scramble) is a scrambled sequence of amino acids 3-20 of SEQ ID NO:1. It is used as a control peptide. SEQ ID NO:3 (R9) consists of nine arginine residues. SEQ ID NO:4 (TAT) is a well-characterized arginine-rich fragment of the HIV transactivator protein. This peptide inhibits activity of several viruses. SEQ ID NO:5 is poly-L-arginine (PolyR) of varying lengths having molecular weights of from about 5000 to 15,000 Da (i.e., lengths of about $R_{28}$ to about $R_{86}$).

HaCaT cells were pretreated with 6 μM concentrations of gp91dstat, gp91dstat (scramble), R9, or TAT, or 3 μM polyR. After 30 minutes of incubation at 37° C., cells were infected with HPV16 pseudovirions (PsVs) at a dose of 300 viral genome equivalents (vge)/cell, and the relative infectivity was quantified after 24 hours compared to infection in untreated cells (FIG. 1). Each treatment was performed in triplicate. Measurements revealed that the most effective inhibition was achieved with 3 μM polyR (>98% inhibition). Treatment with the other arginine-enriched peptides was less effective at blocking HPV infection: gp91dstat caused 92% inhibition, gp91dstat (scramble) led to 85% inhibition, R9 resulted in 66% inhibition, and TAT yielded 44% inhibition.

Figure 2:
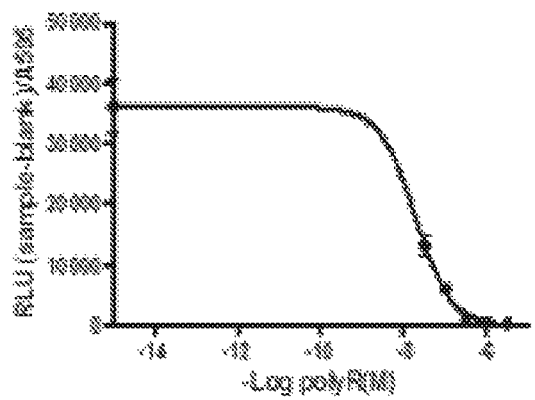
FIG. 2. Fifty percent inhibitory concentration ($IC_{50}$) of HPV16 PsV infection of HaCaT cells by the compounds. For generation of an inhibitory concentration 50 ($IC_{50}$) curves, cells were pretreated with the indicated concentration of arginine-rich peptides prior to HPV16 PsV exposure. Infectivity was scored after 24 hours of incubation at 37° C. and the data from two independent duplicate experiments were pooled and analyzed using non-linear regression (curve fit) function of PRISM software (GraphPad Software, Inc., LaJolla, Calif.). (A) polyR, $IC_{50}$: $1.9 \times 10^{-8}$ M; (B) arginine nonapeptide (R9), $IC_{50}$: $1.55 \times 10^{-6}$ M.
Figure 2:
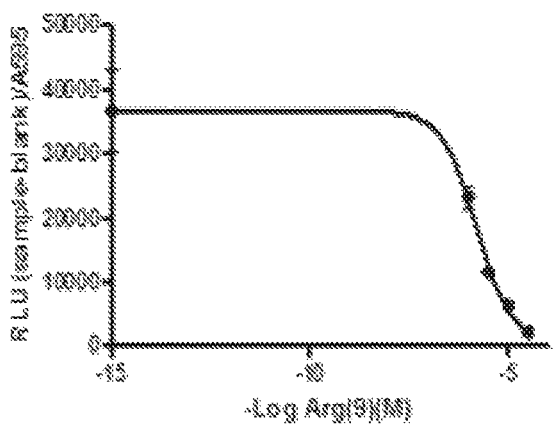

Dose response analyses and inhibitor concentration 50 percent ($IC_{50}$) calculations (FIGS. 2A and 2B) revealed that polyR is a potent inhibitor of HPV16 infection, having an $IC_{50}$ nearly two orders of magnitude lower than that of R9 ($IC_{50}=1.9\times10^{-8}$M versus $1.55\times10^{-6}$ M, respectively).

Figure 3:
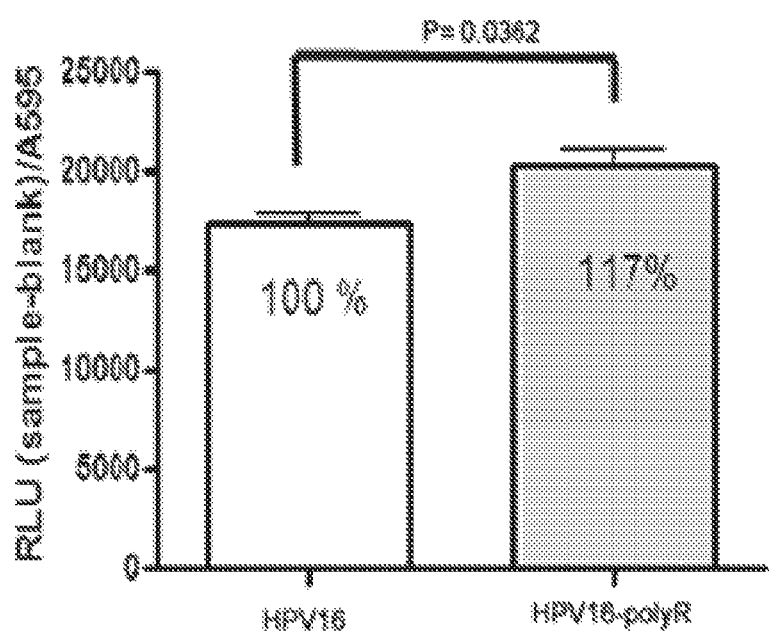
FIG. 3. Direct interaction of polyR with HPV16 does not inhibit infection of HaCaT cells. HPV16 PsVs were incubated with 0.3 µM polyR for one hour at 37° C. The virus-polyR mixture was diluted with CM to reduce the polyR concentration below the $IC_{50}$ value prior to incubation with HaCaT cells for 24 hours (HPV16-polyR). The control included untreated HPV16 PsVs (HPV16) added to HaCaT cells. Infection was measured after 24-hour incubation.

Direct Interaction of polyR with HPV16 does not Inhibit Infection of HaCaT Cells Typically, direct interaction of cationic inhibitors with the viral capsids of non-enveloped viruses (including HPV) is sufficient for antiviral activity. To determine whether polyR inhibited HPV16 infectivity by direct interaction with viral capsids, HPV16 PsVs were incubated with 0.3 polyR for one hour at 37° C. The virus-polyR mixture was diluted 1500-fold to reduce the polyR concentration below the $IC_{50}$ value, then incubated with HaCaT cells. The control included cells exposed to HPV PsVs that were not treated with polyR. FIG. 3 shows that pre-incubation of HPV16 with 0.3 μM polyR did not inhibit infection to a statistically significant degree. Thus, unlike alpha-defensins (a cationic peptide), polyR antiviral activity is not mediated by its direct interaction with the viral capsid.

PolyR Inhibits HPV16 Binding to Host Cells

To determine whether polyR mediated its inhibitory actions on HPV16 by interfering with virus binding to host cells, HaCaT cells were pre-treated with 1 μM polyR for 30 minutes. PolyR-pre-treated cells were incubated with 100 vge/cell HPV16 PsV, at 4° C. for one hour, conditions that allow binding but prevent virus internalization. Control HaCaT cells were left untreated prior to incubation with the same HPV16 PsV dose and conditions. Unbound virus particles were removed with a PBS wash and the remaining cells and bound virus were harvested with lysis buffer (25 mM Tris pH7.5, 100 mM NaCl, 1% Triton X-100 supplemented with protease inhibitors). The amount of the remaining cell-bound virus was analyzed by quantification of the HPV16 major capsid protein L1, after SDS-PAGE fractionation of cell lysates and immuno-blotting.

Figure 4:
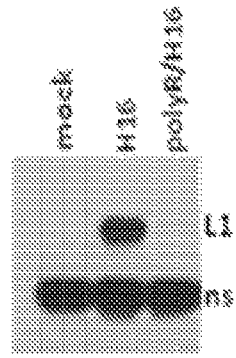
FIG. 4. PolyR treatment of host cells inhibits HPV16 binding to cells. (A) Confluent HaCaT cell monolayers were treated with 1 µM polyR (in CM) for 30 minutes, before adding 100 vge/cell HPV16 PsVs, and incubated at 4° C. for one hour (to promote binding but prevent virus internalization). After washing out of unbound virus, cells were lysed (25 mM Tris pH7.5, 150 mM NaCl, 1% Triton-X100 supplemented with protease inhibitors) and centrifuged at 16,000×g for 10 minutes. Protein concentrations in supernatant were measured using the Bradford method (Bio-Rad Laboratories, Inc., Hercules, Calif.). Samples were boiled in SDS-containing sample buffer, and aliquots containing equal amount of protein (50 g to 200 µg) separated by SDS-polyacrylamide gel electrophoresis (SDS-PAGE), using 10% gel. Proteins were transferred onto polyvinylidene difluoride (PVDF) membranes and subjected to analysis using anti-HPV16 L1 primary antibody (Camvir-1, sc-47699, Santa Cruz Biotechnology, Inc., Dallas, Tex.;1: 5000 dilution) for detection of HPV16 major capsid protein, L1. Proteins were visualized by enhanced chemiluminescence (SUPERSIGNAL West Pico Chemiluminescent Substrate, Thermo Fisher Scientific, Inc., Waltham, Mass.) and exposed to film (Phenix Research Products, Candler, N.C.). (B) Immunofluorescence assays were performed essentially as described previously (Surviladze et al., 2012. PLoS Pathogens 8:e1002519). HaCaT cells were grown on coverslips at approximately 50% confluence and treated with 3 µM polyR for 30 minutes at 37° C. before the addition of 1000 vge of HPV16 PsVs per coverslip. Cells were incubated for one hour at 4° C. and washed several times with PBS, before the fixation with 4% paraformaldehyde (PFA). BSA-blocked cells were incubated with rabbit polyclonal HPV16 antibody (antibody was affinity-purified from rabbit anti-HPV VLP antisera). PBS-washed slides were incubated with donkey AF488-conjugated anti-rabbit IgG secondary antibody; phalloidin-rhodamine (Cytoskeleton, Inc., Denver, Colo.) was used for actin staining. After extensive washing with PBS, cells were mounted in Gold Antifade and immunofluorescent (IF) images were captured by confocal photo-microscopy.
Figure 4:
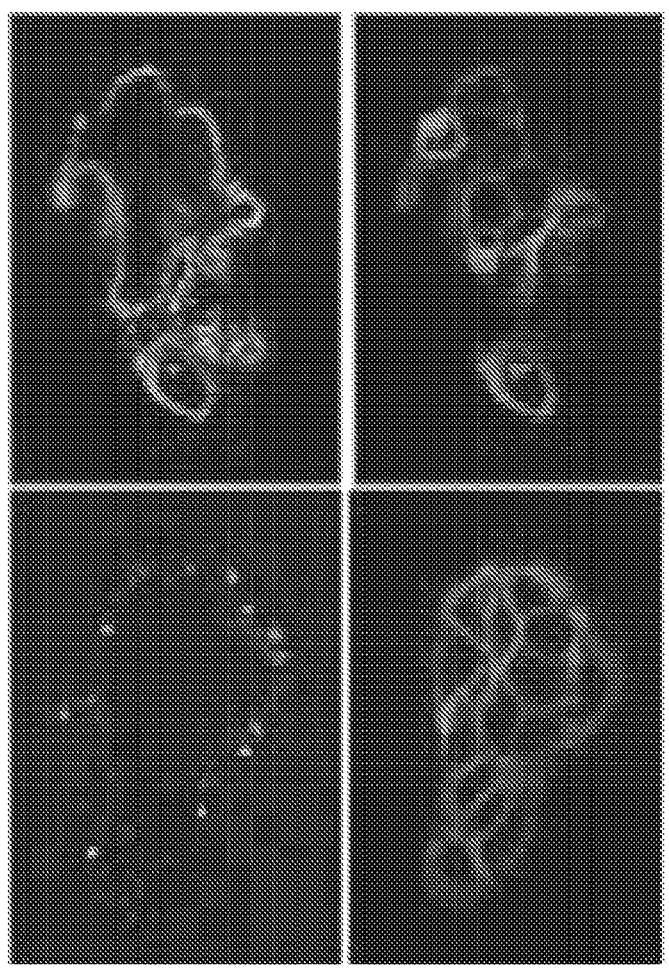

FIG. 4A shows that polyR pre-treatment of cells almost completely blocked HPV16 binding, indicating that polyR inhibits the initial attachment of the virus to the cell surface. Confocal microscopy experiments corroborated the immuno-blot data showing that pre-treatment of HaCaT cells with polyR dramatically reduced detection of HPV bound to the cell surface (FIG. 4B).

Figure 5:
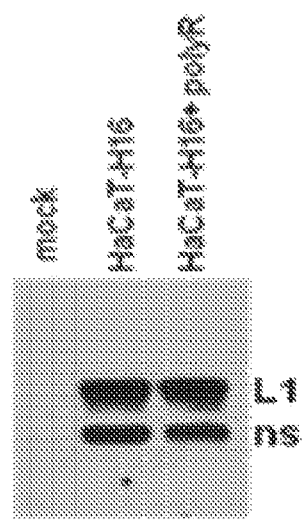
FIG. 5. polyR treatment of HPV-bound cells does not induce virus dissociation from cells. (A) HPV16 PsVs were bound to HaCaT cells (one hour at 4° C.), before the addition of 3 polyR. After a one-hour incubation at 4° C., unbound virus was washed out, cells were lysed and analyzed for the content of HPV L1 protein. (B) HaCaT cells were exposed to HPV 16 PsV at 4° C. in the absence of polyR, simultaneously with polyR (0 h), or one hour after polyR treatment (+1 h). After extensive washing with PBS, cells were lysed and analyzed for the content of HPV16 L1 protein.
Figure 5:
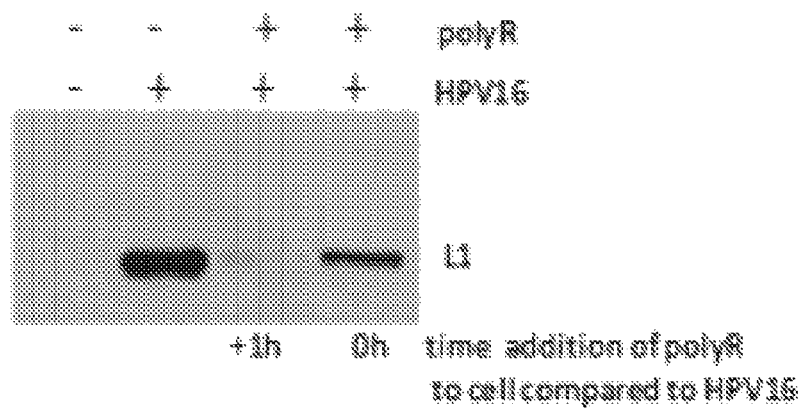

PolyR Treatment of HPV-Bound Cells does not Induce Virus Dissociation from Cells To determine whether polyR could cause HPV16 dissociation from cells, HPV16 PsVs were bound to HaCaT cells for one hour at 4° C. After washing away unbound virus, HPV-bound cells were incubated with 3 μM polyR for one hour at 4° C.; control cells were untreated. Cells were lysed and analyzed for HPV L1 protein content. Immuno-blot analyses revealed that adding polyR to HPV-bound cells did not induce the release of HPV16 from the cell membrane (FIG. 5A). However, when the cells were incubated simultaneously with polyR and HPV, the binding of HPV particles to the cells was reduced by ≈50% compared to cells that were untreated (FIG. 5B). Together, the observations that pretreatment of cells with polyR blocked HPV binding, that polyR was unable to displace cell-bound HPV, and that simultaneous addition of the virus and polyR led to decreased virus binding to cells suggest that polyR and HPV16 have comparable (equivalent) affinities and compete for the virus attachment sites on the cells.

PolyR Affects HPV Infection at Post-Attachment Stages

Figure 6:
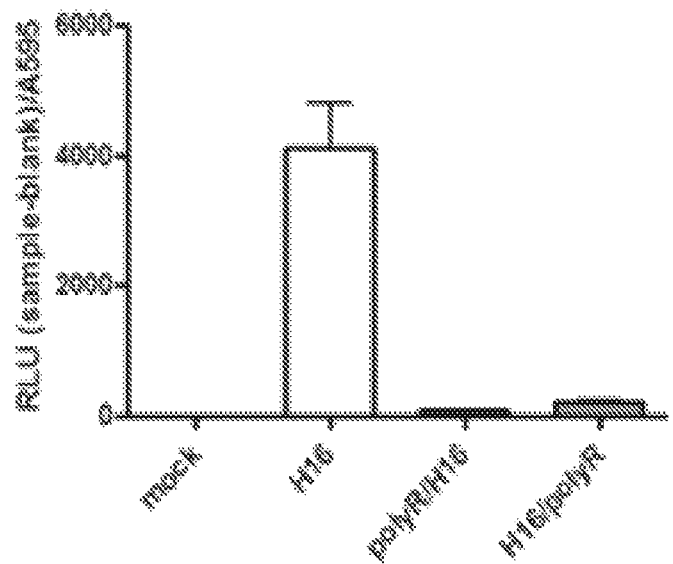
FIG. 6. PolyR inhibits HPV16 PsV infection at pre-attachment and post-attachment stages. (A) Infection of HaCaT cells with HPV16. Semi-confluent HaCaT cells were left untreated with polyR (H16) or exposed to HPV16 PsV 1 h before (polyR/H16) or one hour after 2 polyR (H16/PolyR) treatment, were subjected to infectivity measurements after a 24-hour incubation at 37° C. (as described in FIG. 1). (B) Time-course experiments of HPV infection in the absence or presence of polyR. Untreated control cells were infected with HPV16 PsV (HPV16). HaCaT cells were treated with 1 µM polyR before (+1 h polyR/HPV16), concurrently (0 h polyR/HPV16) or at one hour, two hours, four hours, six hours, or eight hours post-attachment of HPV16 PsVs. Infection was scored at 24 hours post HPV attachment and shift to 37° C.
Figure 6:
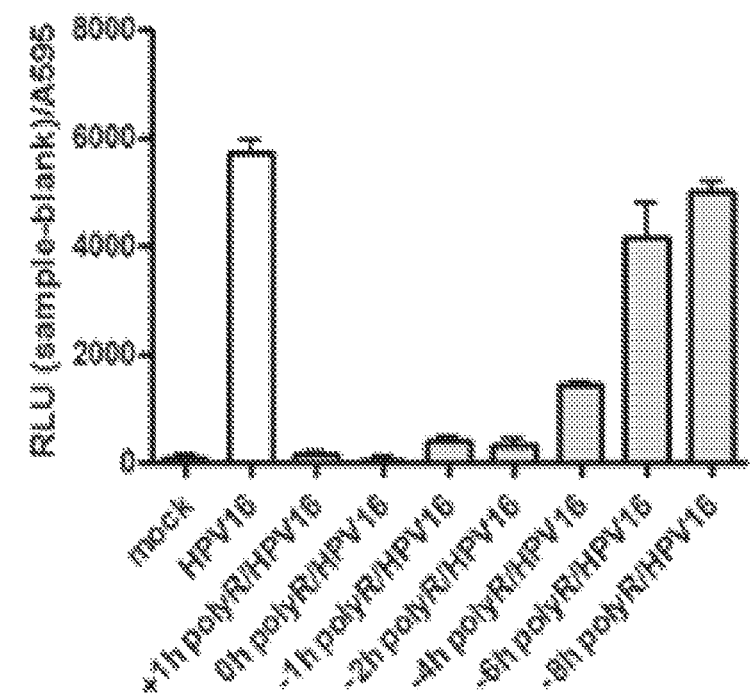

The data above show clearly that polyR can inhibit HPV binding to cells and infection, but that polyR cannot displace HPV after bound to cells. To determine whether polyR can alter HPV infectivity if it is present after HPV is bound to cells, the infection levels of virus-exposed cells that are either pre-treated with polyR before virus binding, polyR-treated after HPV binding, or untreated with polyR were compared. PolyR was as effective at inhibiting HPV infection when added after virus was bound to cells as it was when added prior to virus exposure (FIG. 6A). This indicates a second mechanism whereby polyR can block HPV infection after virus is bound to cells.

Next, the effectiveness of polyR treatment in blocking infection when added at increasing times post HPV binding to cells was tested. This time-course experiment confirmed that polyR affects post-attachment stages of virus infection. HaCaT cells were treated with polyR one hour prior to virus exposure, concurrently with virus exposure, and at increasing times after virus was bound and unbound virus was removed. Infection efficiency was measured after a 24-hour incubation at 37° C. The cells infected with HPV16 PsV in the absence of polyR (FIG. 6B, HPV16) was considered as 100% infection efficiency. Consistent with FIG. 1A, polyR dramatically reduced (>95% inhibition) infection when administered to the cells one hour before cell exposure to the virus (FIG. 6B, +1 h polyR/HPV16). The same magnitude of infection inhibition was observed when polyR and HPV were added simultaneously (0 h polyR/HPV16). Strong infection inhibition continued to occur when polyR was added one hour to two hours post HPV binding and infection (−1 h polyR/HPV16, −2 h polyR/HPV16), and adding polyR four hours post infection (−4 h polyR/HPV16) still led to an approximately 75% reduction in HPV infection. These data demonstrate that cell-bound HPV16 remained susceptible to the inhibitory actions of polyR. Only mild inhibition of HPV16 infection was detected when polyR was added six hours to eight hours post infection.

Figure 7:
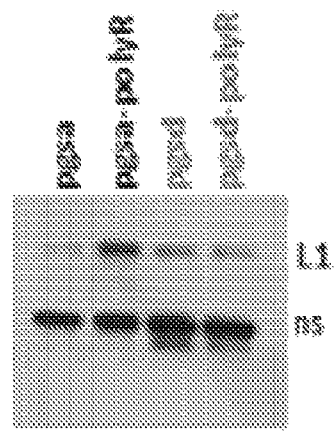
FIG. 7. HPV binding and infection of CHO mutant cells in the presence of polyR. CHO mutant pgsA-745 cells (GAG deficient) and CHO mutant pgsD-677 cells (HS deficient) were grown in Ham's F12 medium supplemented with 10% fetal bovine serum and 1% Glutamax (Invitrogen, Thermo Fisher Scientific, Inc., Carlsbad, Calif.). (A) Cells were incubated with 3 µM polyR in the medium for 30 minutes before adding HPV16 PsVs and incubating at 4° C. for one hour. After extensive washing with PBS, cells were lysed and analyzed for the content of L1, as described in FIG. 4A. (B) Semi-confluent CHO-pgsA were treated with 3 µM polyR for one hour prior to adding HPV16 PsVs. Infection was scored at 24 hours post infection as described in FIG. 1. (C) Semi-confluent CHO-pgsD cells were treated with 3 µM polyR for one hour prior to adding HPV16 PsVs. Infection was scored at 24 hours post infection as described in FIG. 1.
Figure 7:
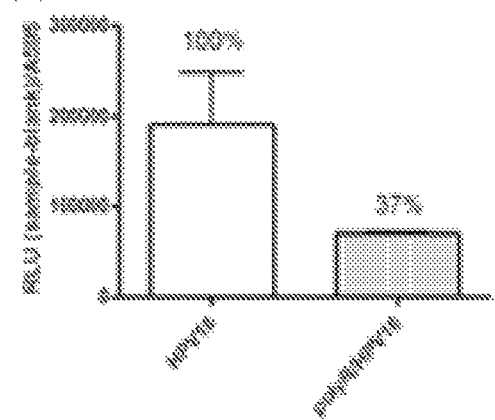
Figure 7:
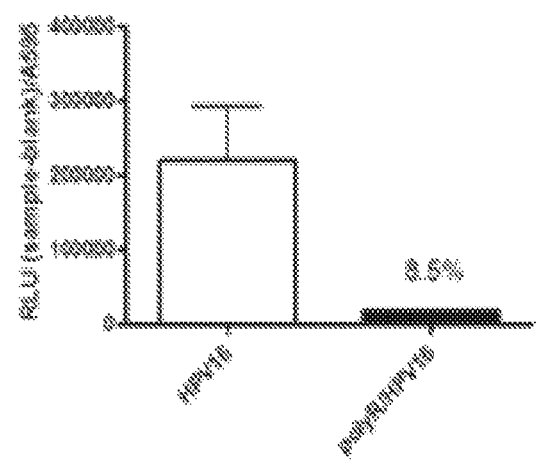

To test the effects of polyR on cells that differentially express heparan sulfate versus heparan sulfonated proteoglycans, like glycosaminoglycans (GAGs), genetically mutant clones of Chinese hamster ovary (CHO) cell lines were used. CHO mutant pgsA-745 cells have a defect in xylosyltransferase, the first sugar transfer in glycosaminoglycan synthesis, and do not produce GAGs, whereas CHO mutant pgsD-677 cells are deficient in the polymerization of heparan sulfate, and do not produce heparan sulfate. First, the effect of polyR on HPV16 PsV binding to these mutant cells was measured. PolyR treatment did not prevent HPV binding to either cell line, and increased binding was observed on pgsA-745 cells (FIG. 7A). However, despite unhindered HPV binding to the GAG- and HS-deficient cells, the infectivity assay showed the presence of polyR significantly reduced HPV16 infection of the pgsA-745 and pgsD-677 cells compared to the respective untreated control cells for each cell line (63% and 92%, respectively, FIG. 7B and FIG. 7C). These data demonstrate that polyR can prevent HPV infection in cells despite the absence of the HS chains or GAGs on the cell surface.

PolyR does not Affect Virus Internalization

Figure 8:
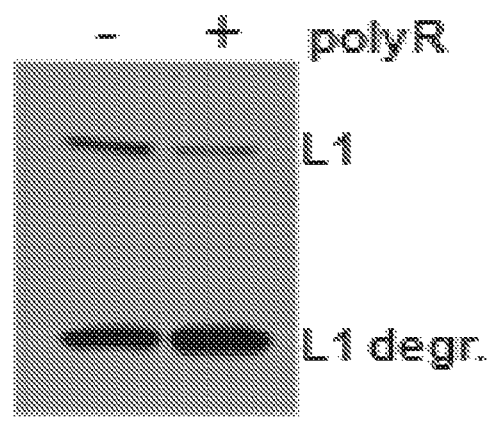
FIG. 8. PolyR reduces the internalization of cell membrane-bound HPV16 PsV. HaCaT cells were incubated with HPV16 PsVs for one hour at 4° C. Unbound virus was removed from the cells by incubation with 0.25% trypsin/5 mM EDTA for 15 minutes at 37° C. Cells were pelleted and washed several times with CM (to neutralize pH) and with ice-cold PBS before adding ice-cold 0.1 M sodium acetate buffer (pH 4.5) containing 0.5 M NaCl. After a two-minute incubation on ice, cells were washed three times with PBS and lysed with RIPA [50 mM Tris (pH 7.5), 0.1% SDS, 1% sodium deoxycholate, 150 mM NaCl, 1 mM EDTA, 1% Triton X-100, 1 mM sodium vanadate, 1 mM PMSF, 10 ng/ml leupeptin, 10 ng/ml aprotinin] buffer. Immuno-blotting was performed, and the L1 protein was detected using a HPV16 L1-specific mAb (Camvir-1, sc-47699, Santa Cruz Biotechnology, Inc., Dallas, Tex.).

To investigate the effect of polyR on the penetration of cell-bound virus into host cells, HPV-bound cells were incubated for four hours in the absence or presence of polyR. Any remaining cell surface attached virus was stripped from cells by incubating cells with 0.25% trypsin/5 mM EDTA for 15 minutes at 37° C. Pelleted cells were washed with ice-cold PBS and treated with ice-cold 0.1 M sodium acetate buffer (pH 4.5) containing 0.5 M NaCl for two minutes at 4° C. Cells were washed three times with PBS and lysed with RIPA buffer. Immuno-blotting was performed, and the L1 protein was detected using a HPV16 L1 specific mAb (Camvir-1; Santa Cruz Biotechnology, Inc., Dallas, Tex.). As HPV16 L1 is proteolytically processed during cell entry, two forms of L1 (full-length 55 kDa and the 25 kDa processed form) were detected. FIG. 8 shows that polyR treatment resulted in decreased levels of 55 kDa L1 protein and increased amounts of the 25 kDa proteolytic processed L1 form internalized in cells. The protein levels in each band were quantified by measuring the pixel intensity of the 55 kDa and 25 kDa L1 bands. The sum of the Integrated Dot Values (IDVs) of these two L1 bands were equal in polyR untreated and treated cells, indicating that polyR had no effect on the virus internalization rate.

Figure 9:
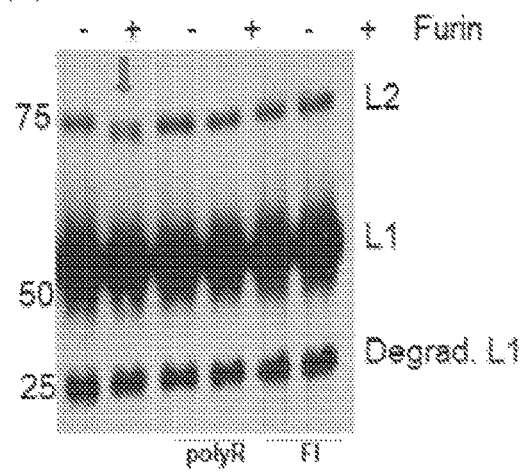
FIG. 9. PolyR inhibits HPV16 L2 protein cleavage by furin and induces accumulation of internalized virus particles in late endosomal fraction. (A) Equal amount of HPV16 diluted in 50 µl furin assay buffer (1 mM $CaCl_2$), 100 mM HEPES, 0.5% Triton X-100, 1 mM β-mercaptoethanol) was loaded into six tubes, and subsequently incubated for two hours at 30° C. without any inhibitor, in the presence of 1.3 µM furin inhibitor1 (Merck Millipore Corp., Burlington, Mass.), or 1 µM polyR. Samples were mixed with SDS-PAGE sample buffer and boiled before fractionation on 9% gel. Proteins were transferred onto PVDF membranes and after blocking, incubated with affinity-purified rabbit anti-HPV16 polyclonal antibody. Secondary donkey anti-rabbit horseradish peroxidase-coupled antibody was used for detection of HPV16 capsid proteins. (B) HaCaT cells grown on coverslips were incubated with HPV16 PsVs for one hour at 37° C. to initiate virus binding (and partial internalization) before adding 1 µM polyR and further incubated for seven hours. After the incubation, cells were fixed and stained for HPV16 and endogenous CD63, using primary anti-HPV16 rabbit polyclonal and anti-CD63 mouse monoclonal antibodies (Santa Cruz Biotechnology, Inc., Dallas, Tex.). PBS-washed slides were incubated with goat anti-mouse-AF555 and donkey AF488-conjugated anti-rabbit IgG secondary antibodies (Invitrogen, Thermo Fisher Scientific, Inc., Carlsbad, Calif.). After extensive washing with PBS, cells were mounted in Gold Antifade, and IF images captured by confocal microscopy. Depicted is a medial single focal plane of representative cells. Co-localization of HPV16 (green) and CD63 (red) is indicated by yellow.
Figure 9:
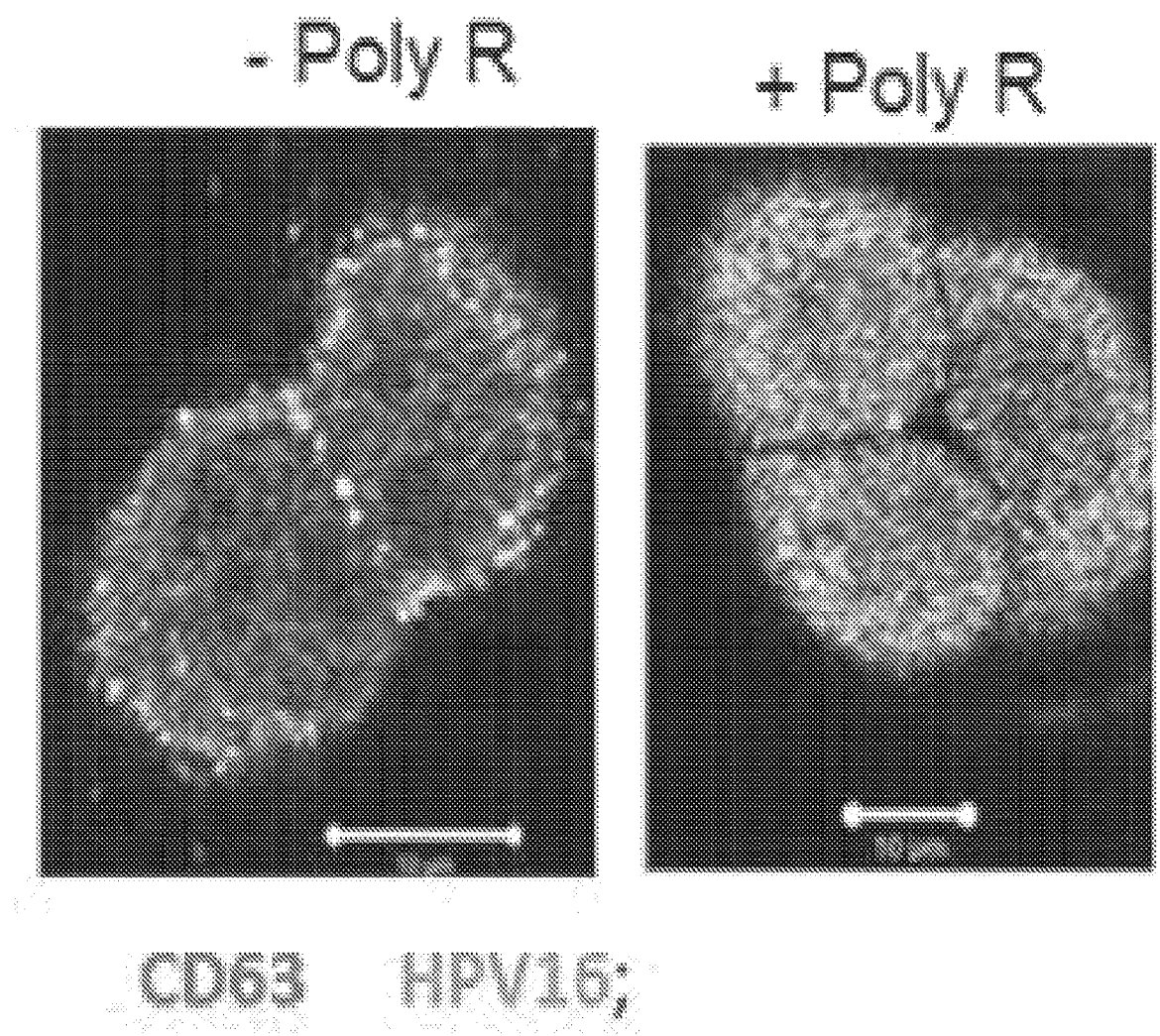

PolyR Induces Furin Inhibition and Accumulation of Internalized Virus Particles in Late Endosomal Fraction Cleavage of the L2 minor capsid protein by the cellular pro-protein convertase, furin, is an essential step in infectious entry of HPVs. Furin cleavage of L2 promotes the egress of the uncoated viral DNA-L2 complexes from the late endosomes and transit of the L2-viral genome complexes to the nucleus to permit gene expression and establish infection. To examine whether polyR inhibits furin activity, purified HPV16 PsVs were incubated with or without 3 nM of recombinant His-furin, in the presence or absence of 1 μM polyR or 30 μM furin inhibitor 1 (FI), at 37° C. After two hours of incubation, HPV16 cleavage was assessed by immunoblotting using anti-HPV 16 polyclonal antibody. FIG. 9A shows that furin cleaves the L2 protein in the absence of polyR and FI. Cleaved L2 (arrow) is visible as a faster-migrating band below uncleaved L2, resulting in the observed doublet band. Treatment of PsVs with furin in the presence of polyR or FI inhibited cleavage of the L2 capsid protein (single band at 75 kDa).

Since biochemical furin inhibitors induce accumulation of HPV in the late endosome, the extent to which the intracellular action of polyR mimicked that of furin inhibition was tested. HaCaT cells grown on coverslips were incubated with HPV16 PsVs for one hour at 37° C. to initiate virus binding (and partial internalization) before 1 µM polyR was added and the cells were incubated for an additional seven hours. Confocal immune-microscopy was used to visualize the localization of HPV16 PsV (green) in endosomes with the endosomal marker protein CD63 (red) in polyR-treated and untreated cells. After the seven-hour incubation of HPV16 in untreated cells, most of the viral capsids were not co-localized with the CD63 endosomal protein (FIG. 9B; left panel). However, treatment with polyR significantly increased co-localization of HPV16 and CD63 (yellow signal indicates overlap of red and green signals), indicating that polyR treatment of cells results in the endosomal accumulation of HPV capsids. These findings are consistent with the activity of polyR in inhibiting the function of furin in processing the L2 molecules (FIG. 9A)

PolyR Inhibits Activity of Authentic HPV16 Virions

Figure 10:
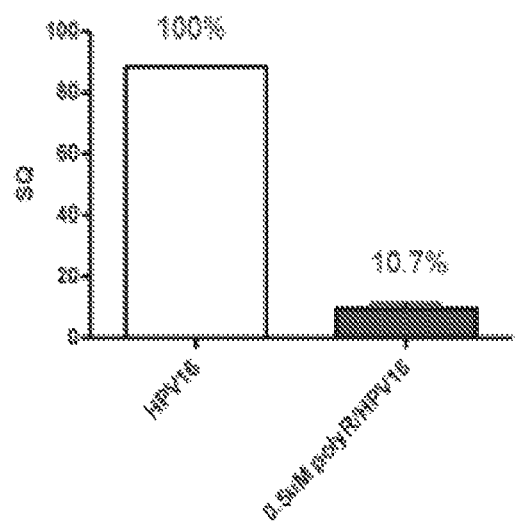
FIG. 10. PolyR inhibits activity of authentic HPV16 virions. HaCaT cells were infected with authentic HPV16 virions (100 vge/cell) in the presence or absence of 500 nM polyR. At three days post-infection, total RNA was extracted from cells using TRIzol reagent (Invitrogen, Thermo Fisher Scientific, Inc., Carlsbad, Calif.). Equal amount of the RNA of polyR-treated and untreated cells was subjected to reverse transcription. Each RT reaction was divided into three qPCR amplifications of 45 cycles targeting the spliced transcripts of cellular β-actin or HPV16 cDNAs. Primers E7.4A and E4B target an amplimer derived from spliced E1^E4 RNA, as previously described (Patterson et al., 2005. J Virol 79:6838-6847).

To validate the effect of polyR was not simply related to pseudovirus infections, HaCaT cells were infected with authentic HPV16 virions carrying viral genomes (100 vge/cell) in the presence or absence of 0.5 µM polyR. At three days post-infection, the cells were harvested and total RNA was extracted using TRIzol reagent (Invitrogen, Thermo Fisher Scientific, Inc., Carlsbad, Calif.). Nucleic acid concentrations were determined by optical density measurements. The RNA of polyR-treated and untreated cells was subjected to reverse transcription as previously described (Ozbun M. A., 2002. *J Virol* 76:11291-11300; Ozbun M. A., 2002. *J Gen Virol* 83:2753-2763). Quantification of cDNA derived from the spliced viral E1^E4 mRNA via qPCR was analyzed in triplicate samples from multiple separate experimental infections. ($\beta$-actin RNAs were also targeted in separate qPCR reactions to normalize data. This RT-qPCR-based infectivity assay revealed strong (~90%) inhibition of HPV16 infection in polyR-pretreated cells (FIG. 10). Thus, data obtained with authentic HPV16 virions are in good agreement with the data obtained with HPV16 PsVs.

PolyR Inhibits HPV16 Infectivity In Vivo

Figure 11:
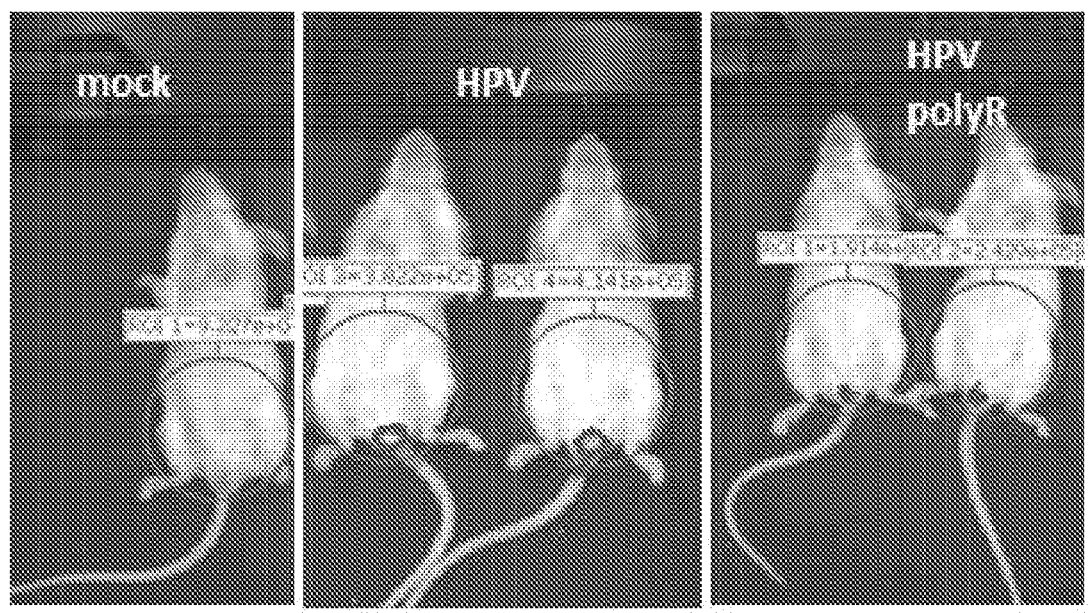
FIG. 11. PolyR inhibits HPV16 infectivity in vivo. (A). Six-week-old to eight-week-old female BALB/c mice were exposed to HPV16 PsVs transducing Luciferase (5×10$^8$ infection units (IU)/animal). (B). Percent of in vivo infectivity represents % of infection calculated from luciferase readouts from panel A. Error bars represents SD n=3. Luciferase raw data (average radiance photons/s/cm$^2$) of polyR-untreated mice is considered as 100%.
Figure 11:
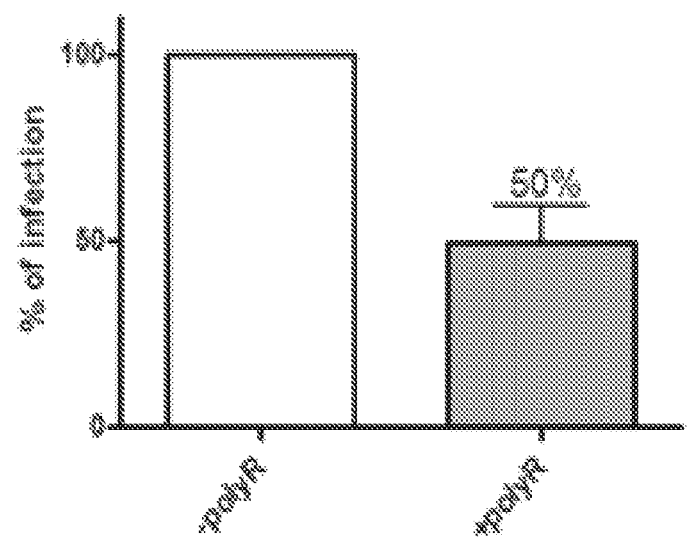

Until recently, in vivo animal studies on infectivity of HPV were problematic, because productive papillomavirus infection is species-restricted and tissue-restricted, and traditional models use animal papillomaviruses in closely related or native host species. However, a recently developed mouse model of cervicovaginal infection using HPV16 PsVs has overcome such restrictions (Roberts et al., 2007. *Nature Medicine* 13:857-861). In the original study, 3% carboxymethylcellulose (CMC) was used to mimic the viscosity of a typical vaginal gel and determined that disruption of genital epithelium by chemical (Nonoxynol-9) or mechanical (using cytobrush) injury is crucial for efficient HPV PsV infection. Nonoxynol-9 (N-9) is a highly toxic strong non-ionic detergent that disturbs the normal architecture of animal and human genital epithelium. The recommended concentration of N-9 (4%) induces significant changes in protein structure and expression in vaginal epithelial cells and thus, may significantly alter the physiologically relevant interaction of HPV with genital cells. For these reasons, mechanical disruption was used to induce abrasions in the murine vaginal epithelium. The experiment was performed as previously described (Roberts et al., 2007. *Nature Medicine* 13:857-861), with slight modifications, using six-week to eight-week-old female BALB/c mice and $5 \times 10^8$ infectious units (IU) of HPV16 PsV conferring expression of a luciferase reporter gene, as previously described (Tyler et al., 2014. *Vaccine* 32:4267-4274). For estrous cycle synchronization, all mice (three control and three experimental) received 3 mg of Depo-Provera (Pfizer, Inc., New York, N.Y.) diluted in 100 µl of sterile PBS in a subcutaneous injection, four days prior to the PsV challenge. For mechanical tissue disruption, the cytobrush (CooperSurgical, Inc., Trumbull, Conn.) was inserted into the vagina of estrous-synchronized mice and twirled clockwise, then counterclockwise, 10 times each. HPV16 PsV inoculum was prepared by mixing PsVs with 3% CMC (for treatment of control mice) or with 3% CMC plus 2 µM polyR (for the experimental group). The final concentration of HPV 16 PsVs was $2.5 \times 10^7$ IU per µl. Ten µl of PsV inoculum was intravaginally inoculated before and six hours after cytobrush treatment. Forty-eight hours after PsV exposure, mice were intravaginally instilled with the luciferase reporter substrate, XenoLight D-Luciferin Potassium Salt (Caliper Life Sciences, Waltham, Mass.), and then subjected to in vivo imaging using an IVIS Lumina II instrument (Caliper Life Sciences, Waltham, Mass.), as previously described (Tyler et al., 2014. *Vaccine* 32:4267-4274). The average radiance per mouse was measured in photons/s/cm$^2$/sr for a set region (of equal dimensions) among mice. Consistent with the in vitro experiments, analysis of the PsV-exposed animals revealed that polyR treatment reduced infection by 50% compared to the animals that did not receive polyR control animals (FIG. 11).

In summary, in vitro studies, using human keratinocyte monolayers and various arginine-rich peptides, revealed that the arginine-rich peptides are potent inhibitors of HPV16 infectivity. Data obtained with HPV16 pseudoviruses were confirmed with authentic HPV16 by in vitro studies on human keratinocyte monolayers and in vivo studies on rodents.

Arginine-rich peptides can effectively inhibit HPV infection by at least two different mechanisms. First, polyR blocks virus binding to attachment factors on the cell membrane. Second, polyR inhibits the essential virus processing with protein convertases, like furin. This means that treatment with polyR may be effective at any time of infection (before, after, or at the time of exposure to HPV). PolyR may be used for prevention of infection, to suppress infection, and/or ameliorate an ailment in infected persons.

While described above in the context of an exemplary embodiment in which the arginine-rich polypeptide is polyR or R9, the arginine-rich can be any suitable arginine-rich polypeptide, as described in more detail below. In many embodiments, the arginine-rich polypeptide can include protamine (e.g., protamine sulfate, PrS). Native salmon protamine (MW 4.1-4.5 kDa) is a cationic (pI 11-13) naturally-occurring antimicrobial peptide, with 50%-80% of its amino acid composition being arginine. The sulfate form of salmon protamine is approved by FDA and is widely used for prolonging the action of insulin and as an antidote against a heparin overdose. Also, protamine is polycationic and therefore electrostatically binds to polyanionic heparin and forms a stable complex that lacks anticoagulant activity. Therefore, salmon protamine is routinely used after cardiac or vascular surgeries to reverse the anticoagulant function of heparin, thereby preventing post-operative bleeding. Protamine sulfate solutions at neutral pH are unstable and tend to precipitate out. Protamine also is widely used for food preservation (to preserve a wide variety of foods).

In some embodiments, the arginine-rich polypeptide may be complexed with an anionic compound. While described below in the context of an exemplary embodiment in which the arginine-rich compound (e.g., PrS) complexes with hyaluronic acid (HA), the compositions and methods described herein can involve complexing any arginine-rich polypeptide with any suitable anionic compound. HA was selected as an exemplary anionic compound because HA is a component of a class of vaginal moisturizers. Adding the arginine-rich polypeptide to these moisturizers results in the formation of an electrostatic (i.e., no cross-linking) complex with HA (e.g., an HA:PrS complex). Thus, the data reported herein establish that an exemplary arginine-rich polypeptide, PrS, retains microbicidal activity when complexed with an anionic compound.

Protamine sulfate (PrS), whether alone or in the HA:PrS complex form, is a relatively inexpensive antimicrobial compound, is FDA approved, is widely used in various fields of medicine, and is stable in acidic conditions such as are typical present in the vagina. Thus, topical application of an HA-containing vaginal gel with a low concentration of protamine (e.g., up to 2 µM) are safe and can inhibit HPV infection. Moreover, PrS and HA:PrS dramatically inhibits expression of HPV16 vital proteins in vitro. Therefore, a PrS-containing gel can be used as a therapeutic treatment option for HPV-infected individuals.

Since PrS traditionally is used as a food preservative, using PrS will allow manufacturers to avoid/or reduce the concentration of toxic and much more expensive preservatives (e.g. parabens) frequently used in moisturizers.

Vaginal dryness is prevalent among women of all ages but is particularly common during and after the menopause. Approximately 15% of premenopausal and up to 57% of postmenopausal women experience this condition. Natural lubrication of the vagina is produced by glands at the cervix. The vaginal moisture is slightly acidic, which helps to keep the area healthy, therefore it generally desirable to maintain a low pH (3.5 to 4.5). Estrogen promotes, among other things, production of moisture from the cervix. However, estrogen levels fall at the menopause, causing many postmenopausal women to experience vaginal dryness, a painful condition with itching and burning symptoms. Menopause is not, however, the only reason for the vaginal dryness, since estrogen decline can be associated with many other factors including, but not limited to, breast feeding, childbirth, nicotine dependence, primary immunodeficiency, perimenopause (the transition time before menopause), oophorectomy (ovary removal surgery), use of allergy and cold medications or anti-estrogen medications, diabetes, obesity, autoimmune disorders, the use of certain medicines (e.g. antidepressants, antihistamines), radiation or chemotherapy, extreme stress or excessive exercise, anxiety, and/or irritants to delicate tissues Women who experience problems with vaginal lubrication due to hormonal changes often benefit from estrogen therapy. Estrogen-based products could be taken orally, applied topically on the skin, or directly in vagina. Estrogen therapy is associated with risks, however, including elevated risks of developing breast cancer, endometrial cancer, uterine cancer, liver failure, venous thromboembolism, myocardial infarction, and/or stroke. Accordingly, many patients prefer to avoid estrogen-based therapies.

Lubricants are designed to coat the vagina for immediate relief. Commercially available lubricants are water-based, silicone-based, or oil-based. In contrast to lubricants, vaginal moisturizers are absorbed into the skin and exert their effects by replacing normal vaginal secretions. Moisturizers can be taken regularly for treatment of chronic vaginal dryness and can help in decreasing vaginal dryness symptoms (e.g. irritation, sensitivity, soreness and painful sexual activities). Some vaginal products claim to be both a vaginal moisturizer and a vaginal lubricant.

Products designed for vaginal use must not negatively impact the vaginal environment and survival of lactobacilli. Lactobacilli compete with other microbes for nutrients, and secrete factors, such as lactic acid, that make the environment inhospitable to other bacteria and pathogens. Vaginal moisturizers can be grouped into several categories according to the function of their main active ingredients: bioadhesive vaginal moisturizers (e.g., REPLENS, Church & Dwight Co., Inc., Trenton, N.J.; REPHRESH, Church & Dwight Co., Inc., Trenton, N.J.; K-Y liquibeads, Johnson & Johnson, New Brunswick, N.J.), hyaluronic-acid-based vaginal moisturizers (e.g., HYALO GYN, Fidia Pharma USA, Parsippany, N.J.; HYALOFEMME, Fidia Pharma USA, Parsippany, N.J.), and prebiotic vaginal moisturizers (e.g., LUVENA, Laclede, Inc., Rancho Dominguez, Calif.).

The prevalence rate of HPV in the cervix or vagina of postmenopausal women can be comparable to the rate seen in women up to 25 years old. Vaccinating postmenopausal women against HPV is ineffective because the approved HPV vaccines work only when administered in early teenage (or pre-teenage) years. Thus, there is a need for development of broad-spectrum antiviral compounds that might be used as topical microbicide to decrease the sexual transmission of HPV.

Salmon protamine is an arginine-rich polypeptide generally present in the form of protamine sulfate (PrS). While described below in the context of exemplary embodiments in which the protamine sulfate includes salmon protamine (e.g., SEQ ID NO:9), the protamine can be obtained from any suitable source and, therefore, includes any protamine expressly listed herein (SEQ ID NO:6-13), protamine from any other species, or a protein that is produced recombinantly or any by any other non-biological process that is structurally similar to a protamine.

To evaluate the anti-HPV activity of PrS, HaCaT cells, a keratinocyte-derived cell line, was used as a model for analysis of HPV infection. HaCaT cells were grown as reported previously (Surviladze et al., 2012., *PLoS pathogens* 8: e1002519). All 37° C. incubations were in 5% $CO_2$.

Infections were initiated using Luciferase-expressing HPV16 PsVs that were produced, isolated, and quantified as described previously (Surviladze et al., 2012. *PLoS Pathogens* 8: e1002519; Campos S K and Ozbun M A, 2009. *PloS One* 4:e4463). For infection studies, low concentration of virus PsVs (at 50-150 viral genome equivalents per cell (vge)) were used, but in experiments to estimate inhibitory effect of protamine, high concentration of HPV16 PsVs (300-500 vge/cell) were used. Cell monolayers were treated with various concentrations of PrS dissolved in complete cell growth medium (CM) 1 h prior the addition of HPV16. Cells incubated in $CO_2$ incubator at 37° C. and infection was quantified 24 hours post exposure as reported previously (Surviladze et al., 2012. *PLoS Pathogens* 8: e1002519). Raw data were normalized to total cellular protein concentration.

Figure 12:
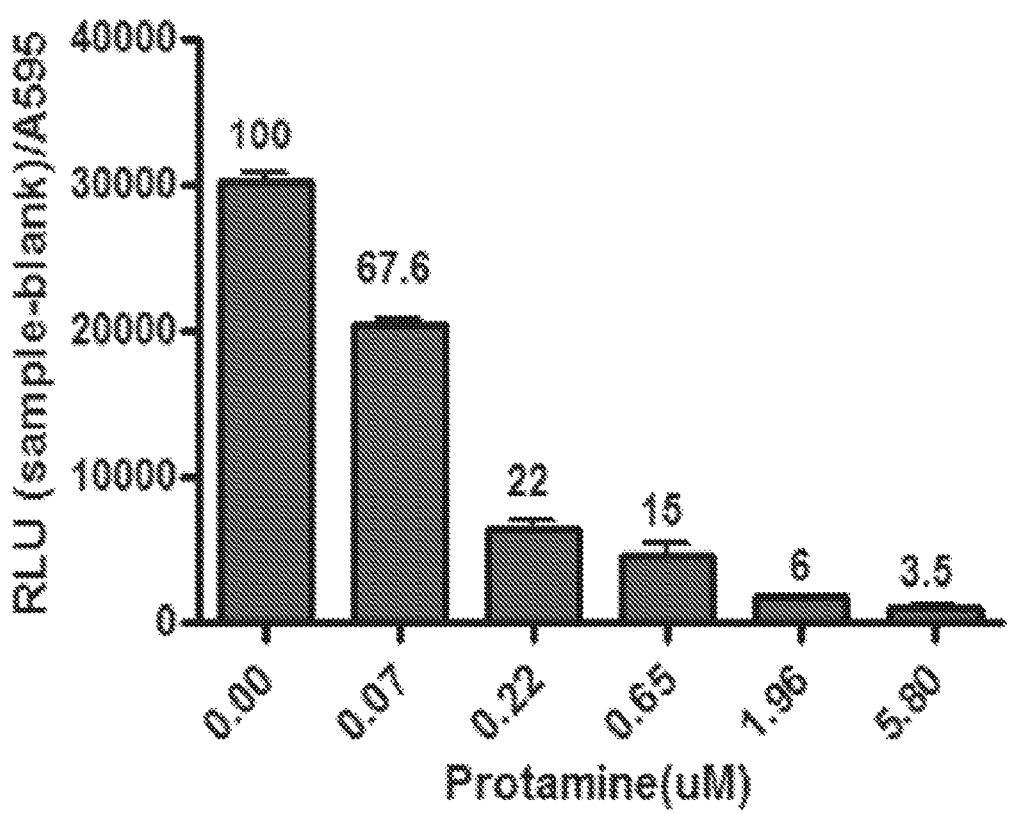
FIG. 12. Inhibition of HPV16 infection with protamine sulfate (PrS). Semi-confluent HaCaT cells maintained in CM, were pretreated for one hour with PrS dissolved in CM at the 0-5.8 µM concentrations before exposure to HPV16 PsVs (350 vge/cell). Infectivity was scored after 24 hours of incubation at 37° C. using a luminometer (Lumat LB9501, Berthold GmbH & Co., Bad Wildbad, Germany) and luciferase assay (Promega, Madison, Wis.) according to manufacturer's specification. Raw data were normalized to total cellular protein concentration.
Figure 13:
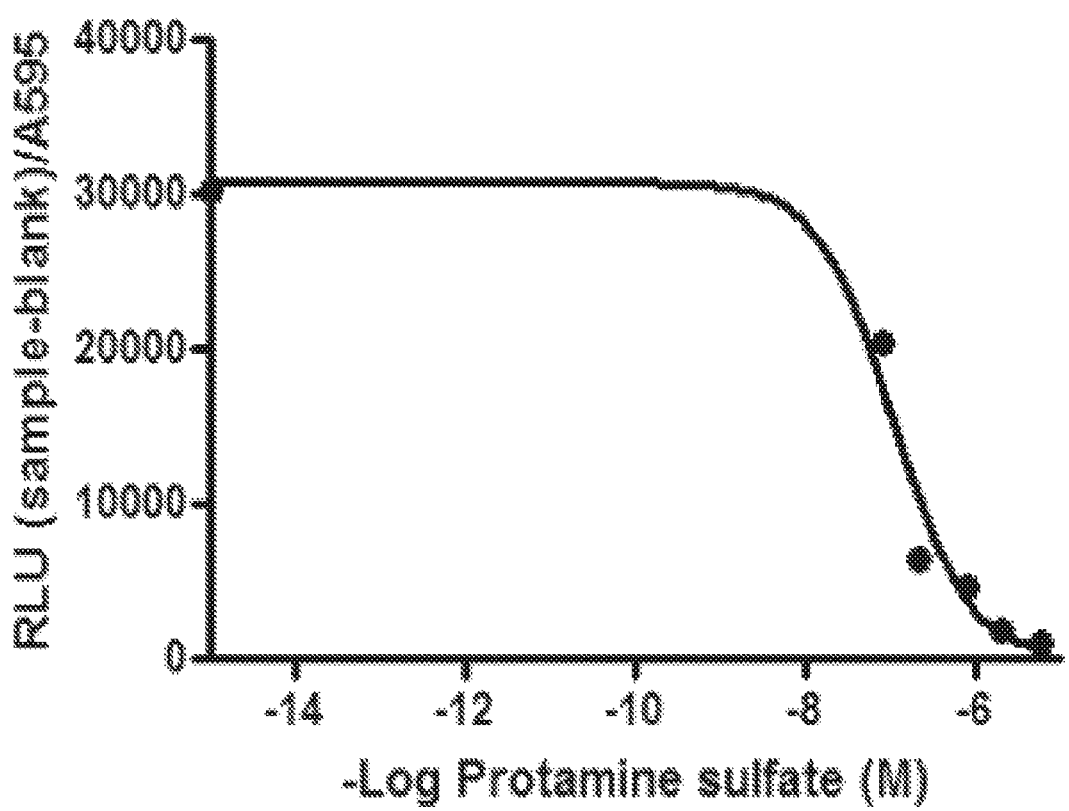
FIG. 13. For generation of an inhibitory concentration 50 ($IC_{50}$) curve for PrS inhibition, data from two independent duplicate experiments was pooled and analyzed using the non-linear regression (curve fit) function of PRISM (GraphPad Software, Inc., La Jolla, Calif.).
Figure 14:
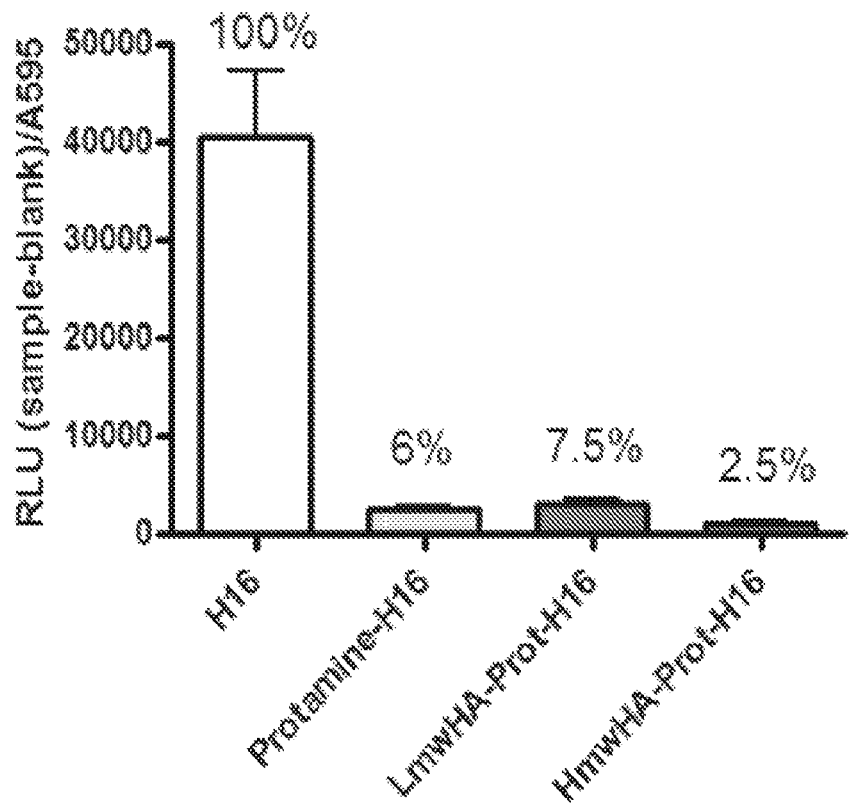
FIG. 14. Effect of HA:PrS complex on HPV16 infection. 3 µM PrS incubated for one hour at room temperature with 2 mg/ml high or low molecular weight HA in CM, prior to the addition to HaCaT cells. 350 vge/cell HPV16 PsVs were used for infection of cells in the presence or absence of PrS or HA:PrS complex. Infection was scored after 24 hours as described in FIG. 12.
Figure 15:
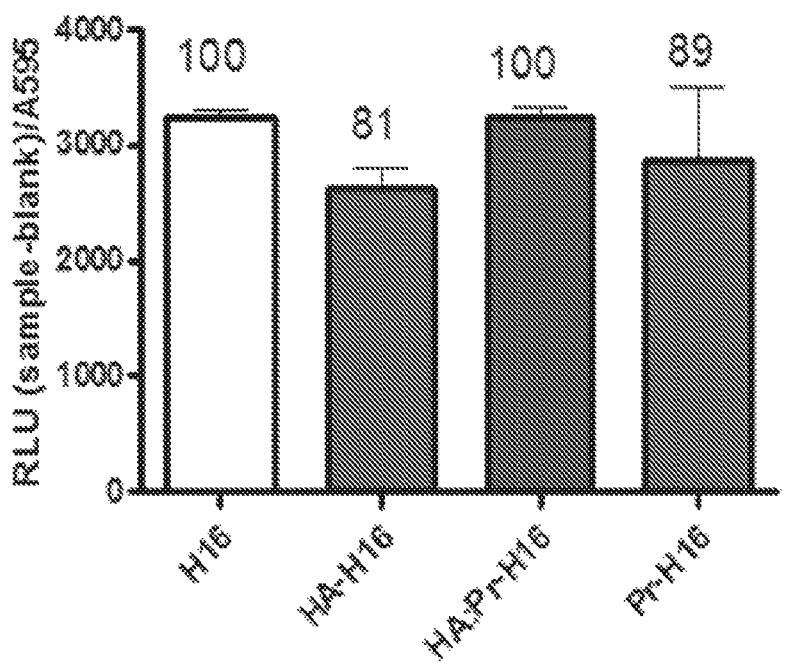
FIG. 15. Direct interaction of PrS to HPV16 PsVs. HPV16 PsVs were incubated with 1 µM PrS or HA:PrS complex for one hour at 37° C. Virus-PrS/or HA:PrS mixture was diluted with CM in order to reduce the PrS concentration below the $IC_{50}$ value, and incubated with HaCaT cells for 24 hours. The control included untreated HPV16 PsVs. Infection was measured after 24 hours incubation as described in FIG. 12.
Figure 16:
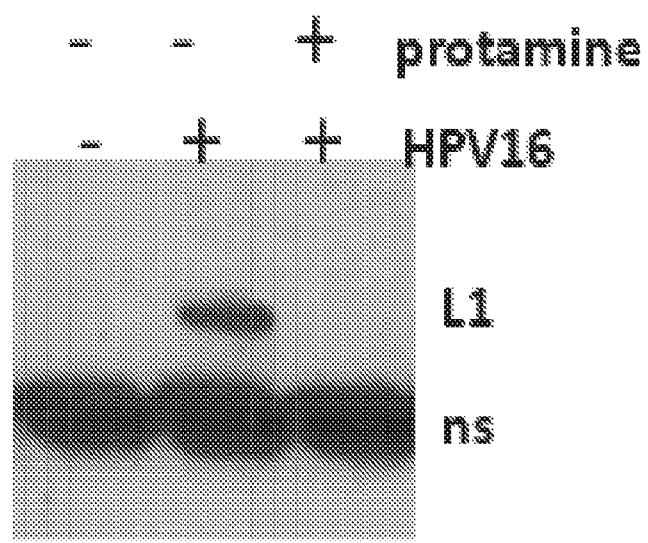
FIG. 16. PrS pretreated cells binding of HPV16. Confluent HaCaT cell monolayers were treated with 1 µM PrS (in CM) before the addition of 200 vge/cell HPV16 PsVs and incubated at 4° C. for one hour (conditions to prevent virus internalization). After washing out of unbound virus, cells were lysed (25 mM Tris pH7.5, 150 mM NaCl, 1% Triton-X100 supplemented with protease inhibitors) and centrifuged at 16,000×g for 10 minutes. Protein concentrations in supernatant were measured using the Bradford method (Bio-Rad Laboratories, Inc., Hercules, Calif.). Samples were boiled in SDS-containing sample buffer, and aliquots containing equal amount of protein (~50 µg to 200 µg) separated by SDS-polyacrylamide gel electrophoresis (SDS-PAGE) using 10% gel. Proteins were transferred onto polyvinylidene difluoride (PVDF) membranes and subjected to analysis using anti HPV16 L1 primary antibody (Camvir-1, sc-47699 Santa Cruz Biotechnology, Inc., Dallas, Tex.; 1:5000 dilution) for detection of HPV16 major capsid protein. Proteins were visualized by enhanced chemiluminescence (SuperSignal West Pico Chemiluminescent Substrate, Thermo Fisher Scientific, Inc., Waltham, Mass.) and exposed on film (Phenix Research Products, Chandler, N.C.).
Figure 17:
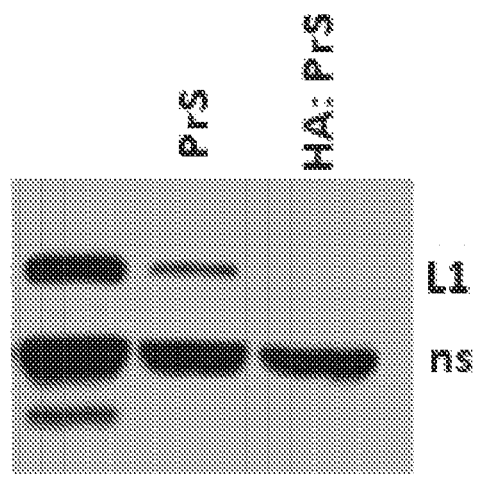
FIG. 17. Binding of HPV to cells at acidic conditions in the presence of PrS. HaCaT cells were incubated with 20 mM sodium lactate pH 4.5 buffer supplemented with 150 mM NaCl for 30 minutes in the presence or absence of 2 µM PrS or 0.1% HMW HA:2 µM PrS complex, before addition of HPV16 PsVs (~100 vge/cell). (A) Cells were incubated one hour at 4° C., unbound virus washed out (with sodium lactate buffer and PBS) and lysed with 1% Triton X-100 containing 20 mM Tris pH7.5, 150 mM NaCl buffer supplemented with protease inhibitors. (B) Amount of bound L1 protein visualized and quantified as described FIG. 16.
Figure 17:
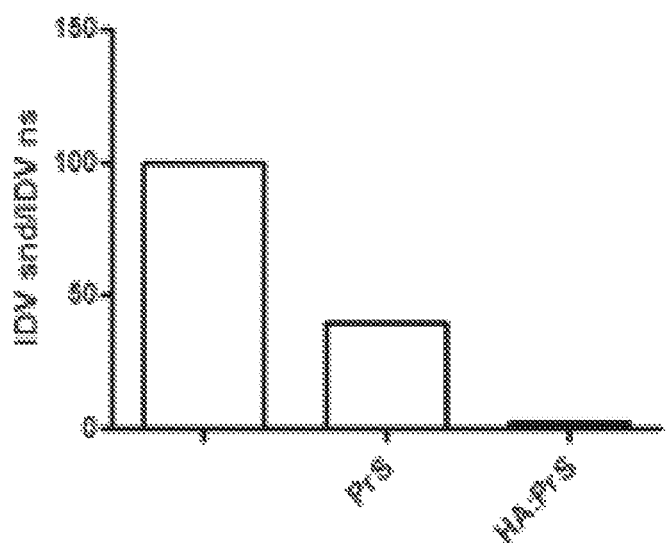
Figure 18:
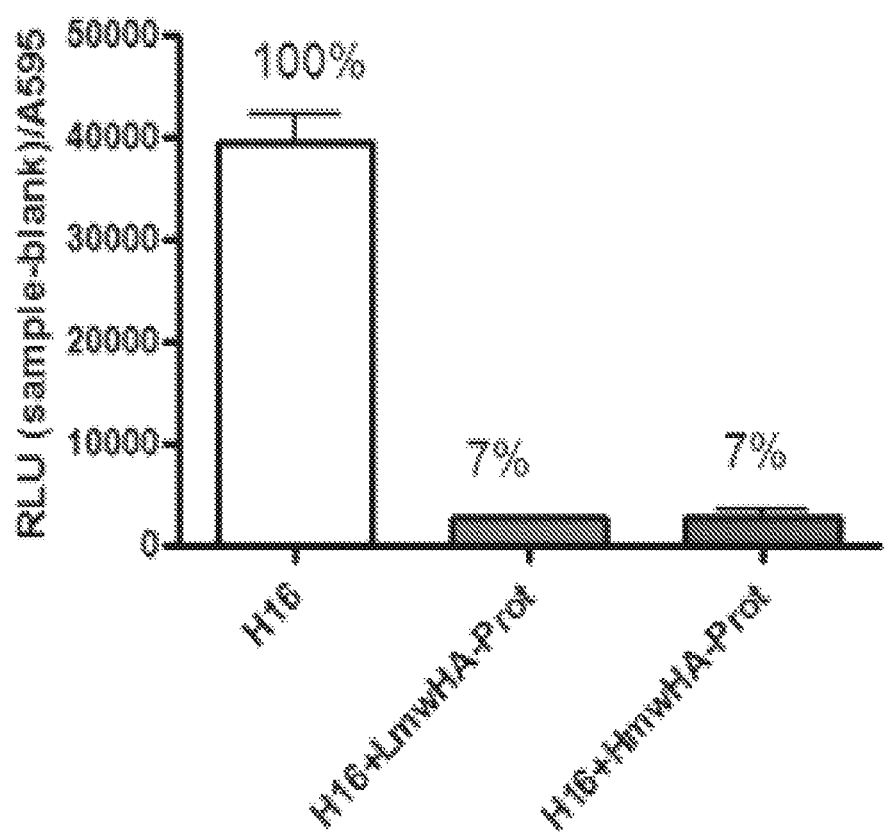
FIG. 18. PrS post-attachment effect on HPV infection. HaCaT cell were incubated with 500 vge/cell HPV PsVs at RT for one hour before addition of 1.5 µM PrS complexed with 0.1% HMW HA or with 3 µM LMW HA. Infection scored 24 after infection as described in FIG. 12.
Figure 19:
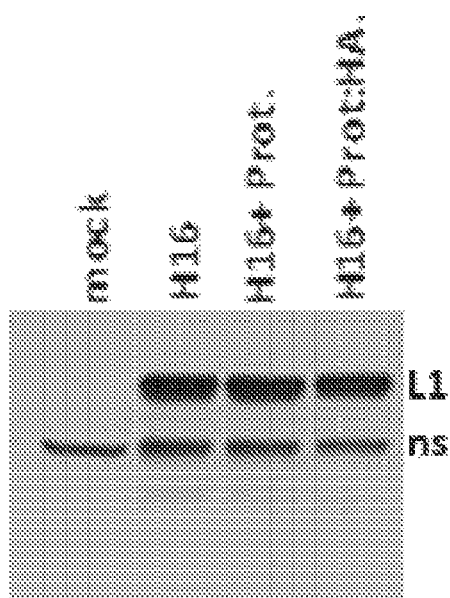
FIG. 19. Addition of PrS to HPV-bound cells did not induce HPV16 release from membrane. HPV16 PsVs were bound to HaCaT cells (one hour in cold), before the addition of 5 µM PrS. After a one-hour incubation at 4° C., unbound virus was washed out, cells were lysed, and HPV L1 protein content was measured as described in FIG. 16.
Figure 20:
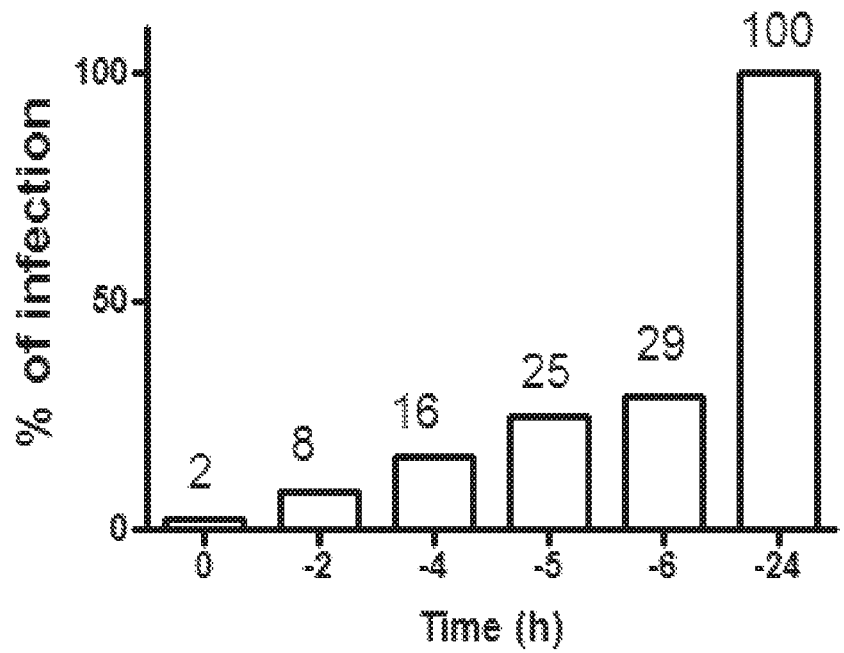
FIG. 20. Time-course experiments of HPV infection in the presence of PrS or HA:PrS complex. (A) PrS; (B) HA:PrS complex. HaCaT cells were treated with 2 µM PrS or 2 µM PrS associated with 0.1% HMW HA at indicated times post-attachment of HPV16 PsVs, and infection was scored 24 hours after infection as described in FIG. 12. Time-point zero represents initial PsV inoculation.
Figure 20:
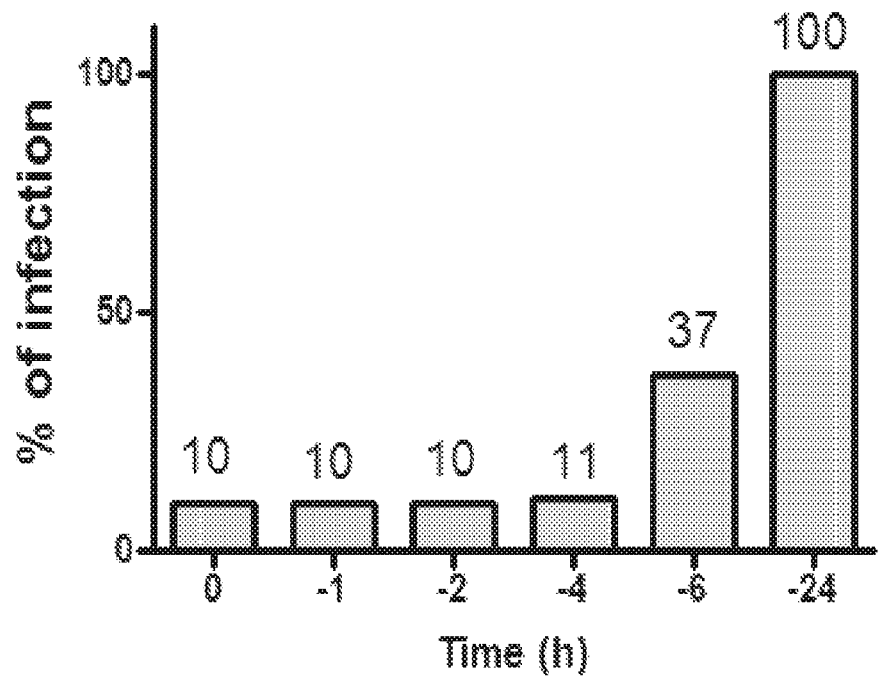
Figure 21:
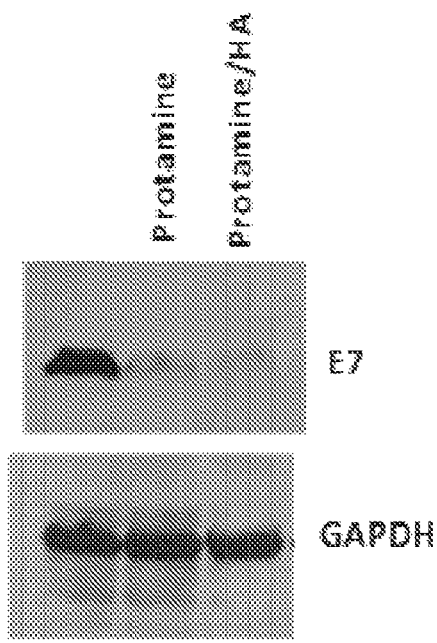
FIG. 21. PrS effect on late stages of infection. HPV16-positive SG3 cells were cultured in E-media supplemented with 10% fetal bovine serum. Semiconfluent monolayer of cells incubated with or without 1 µM PrS or HA:PrS complex in E-medium. After a 24-hour incubation, cells were extracted in RIPA buffer (150 mM NaCl, 1% Nonidet P-40, 0.5% deoxycholate, 0.1% SDS, 50 mM Tris-HCl pH 7.5 supplemented with PMSF). Cell lysates were cleared by centrifugation at 16,000×g for 10 minutes at 4° C. Cell lysates were fractionated on 4-20% gradient gels (Mini-PROTEAN gels, Bio-Rad Laboratories, Inc. Hercules, Calif.), transferred on PVDF membrane and analyzed on content of HPV16 E7 protein and GAPDH (as loading control). Primary antibodies were used at the following dilutions: antibody against HPV 16 E7 (sc-6981, Santa Cruz Biotechnology, Inc., Dallas, Tex.) was used at 1:1000 dilution; and anti GAPDH (Thermo Fisher MA5-15738, Thermo Fisher Scientific Inc., Waltham, Mass.) 1:10 000; Appropriate secondary anti-mouse horseradish peroxidase-conjugated antibody was used (1:3,000; Amersham, GE Healthcare Life Sciences, Pittsburgh, Pa.) for detection of proteins. Integrated dot values of E7 and GAPDH detected using AlphaEaseFC software (Informer Technologies, Inc., Los Angeles, Calif.), and IDV E7 ratio to IDV GAPDH used for data normalization.
Figure 21:
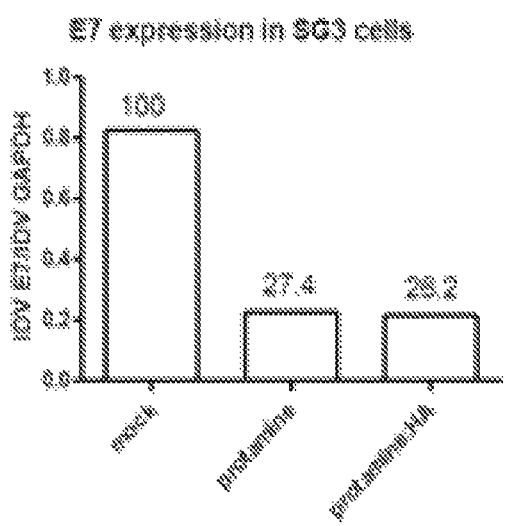

Protamine sulfate inhibited HPV16 infection of HaCaT cells (FIG. 12). For generation of an inhibitory concentration 50 ($IC_{50}$) curve for PrS inhibition, data from two independent duplicate experiments were pooled and analyzed using the non-linear regression (curve fit) function (FIG. 13). The concentration curve demonstrate that protamine sulfate is a high potency inhibitor of HPV16 infection in HaCaT cells ($IC_{50}$~100 nM).

Polycationic PrS can electrostatically bind polyanionic HA. Forming a complex between protamine sulfate and hyaluronic acid can neutralize cationic charges of PrS and change their properties (e.g., HPV16 infection inhibition). To evaluate the effect of HA:PrS complex on HPV infection of HaCaT cells, PrS was incubated with high and low molecular weight HA in CM, at room temperature (RT) for one hour prior to being added to HaCaT cells. Concentrations of both forms of HA (sodium salts of HA from *Streptococcus equi*, Sigma-Aldrich, St. Louis, Mo.) were 2 mg/ml in CM. Molecular weights:15-30 kDa, and 1500-1800 kDa for low molecular weight and high molecular weight forms of HA, respectively; HPV16 PsVs (~350 vge/cell) were used for infection of cells in the presence or absence of PrS or HA:PrS complex. Infection scored after 24 hours showed that the HA:PrS complex efficiently (>90%) inhibited HPV16 infection (FIG. 14).

Several cationic peptides can bind directly to the viral capsids of non-enveloped viruses (including HPV16) and efficiently inactivating their infectivity. To determine whether direct interaction of PrS with HPV16 is responsible for inhibiting viral infectivity, HPV16 PsVs was incubated with PrS or HA:PrS complex for one hour at 37° C. Virus-PrS or virus-HA:PrS mixture was diluted with CM in order to reduce the PrS concentration below the $IC_{50}$ value, and incubated with HaCaT cells. The control included untreated HPV16 PsVs. This infectivity assay revealed that PrS or HA:PrS pre-incubation with HPV16 does not inhibit infection (FIG. 15). This result indicates that direct interaction of PrS to virus is not the reason of HPV infection inhibition.

To detect whether PrS treatment blocks HPV binding sites, HaCaT cells were treated with 1 μM PrS (in CM) before the addition of HPV16 PsV and incubation at 4° C. for one hour. Western blot analysis for HPV16 L1 protein revealed that PrS pretreatment of the cells almost completely blocked HPV16 binding, indicating that PrS inhibits the initial attachment of virus to the cell surface (FIG. 16).

Human vaginal pH is acidic, therefore the binding of HPV16 to cells was examined at pH 4.5. FIG. 17 shows that PrS and HA:PrS complex remained effective for inhibiting HPV16 binding to keratinocytes under acidic conditions. Normalized data shows 60% inhibition in the presence of 2 μM PrS and >97% inhibition with HA:PrS.

To investigate PrS post-attachment effect on infection, HaCaT cell were exposed with HPV PsVs at room temperature for one hour before addition of PrS complexed with heavy molecular weight (HMW) HA or with low molecular weight (LMW) HA. Infection scored after 24 hours post-infection shows >90% inhibition of infectivity with both HA:PrS complexes (FIG. 18).

The post-attachment inhibitory effects of PrS could be due the displacement of capsids from the cell surface. To investigate this possible mechanism, HPV16 PsVs were bound to HaCaT cells (one hour in cold) before adding access concentration of PrS. After a one-hour incubation at 4° C., unbound virus was washed out, cells were lysed, and the HPV L1 protein content was analyzed. Western blot analyses revealed that adding PrS to HPV-bound cells did not induce HPV16 release from membrane (FIG. 19).

This result shows that the PrS-induced inhibition of HPV pre-bound cells is not due the prevention of virus binding, and in addition to blocking the initial attachment of virions to cells, PrS also exerts a post-attachment inhibitory effect on infectivity. Time-course experiments in which HaCaT cells were exposed to PrS or PrS:HA complex at various times after attachment with HPV16 PsVs confirmation this mechanism. A representative experiment is shown in FIG. 20, demonstrating (a) that cell-bound HPV16 remained susceptible to inhibition by PrS and (b) adding inhibitor after six hours post-binding resulted in >60% inhibition of infection.

To examine the effect of PrS on late stages of infection, an HPV-infected cell line (cell line derived by HPV16 DNA transfected spontaneously immortalized human keratinocyte cell line NIKS-SG3cells) was used. This cell line expresses HPV16 oncoproteins E6 and E7, which are necessary for induction and maintenance of the transformed phenotype. These oncoproteins have neither enzymatic nor specific DNA binding activities, and function by perturbing host cellular regulatory networks. For example, E7 protein binds and induces the degradation of the hypophosphorylated form of the retinoblastoma tumor suppressor protein (pRB), causing persistent activation of E2F transcription factors. This results in aberrant S-phase entry. In addition, the HPV E7 disrupts the intimate association between cellular differentiation and proliferation in normal epithelium, allowing for viral replication in cells that would no longer be in the dividing population. This function is directly reflected in the transforming activities of E7, including tumor initiation and induction of genomic instability.

To examine the effect of PrS/or PrS:HA complex on E7 expression in HPV16-positive cells, semi-confluent monolayers of SG3 cells were used. In three independent experiments, a considerable decrease of E7 oncoprotein expression after incubation of SG3 cells with 1 μM PrS or HA:PrS complex (representative of these experiments is shown in FIG. 21). Normalized data showed that inhibition level ranged from 30 up to 70% inhibition compared to Prs-untreated cells.

While described above in the context of an exemplary embodiment in which PrS inhibits HPV infection, the compositions and methods described herein can involve inhibiting infection by various fungal, bacterial. and viral species. PrS can inhibit infection by, for example, bacteria such as, for example, *Bacillus subtilis, Bacillus cereus, Listeria monocytogenes, Salmonella Typhimurium, Escherichia coli, Staphylococcus epidermidis*, other oral pathogenic bacteria, and/or foodborne bacteria; yeasts such as, for example, *Candida utilis*; and viruses such as, for example, Hepatitis A, Hepatitis B, Semliki Forest virus, Encephalomyelitis virus, Human papilloma virus (e.g., HPV-11), Vesicular stomatitis virus, Coxsackievirus (e.g., CV-A9), Human parechovirus (e.g., HPeV-1), and Norovirus.

Thus, in one aspect, this disclosure describes compositions that include an amount of an arginine-rich polypeptide—either alone or complexed with an anionic compound—effective to inhibit infection. For example, the arginine-rich polypeptide may be added to conventional vaginal moisturizers to provide microbicidal activity, particularly anti-HPV activity.

In a second aspect, this disclosure describes a method of inhibiting a human papillomavirus (HPV) from binding to a cell. Generally, the method includes treating the cell with an amount of an arginine-rich polypeptide effective to inhibit HPV binding to the cell.

In a third aspect, this disclosure describes a method of inhibiting intracellular processing of human papilloma virus (HPV) by a cell. Generally, the method includes treating the cell with an amount of an arginine-rich polypeptide effective to inhibit intracellular processing of HPV by the cell.

In a fourth aspect, this disclosure describes a method of treating a subject having, or at risk of having, a human papillomavirus (HPV) infection. Generally, the method includes administering to the subject an amount of an arginine-rich polypeptide effective to ameliorate at least one symptom or clinical sign of infection of infection by HPV.

In all aspects, an arginine-rich polypeptide, as described herein, is a polypeptide that includes at least 10% arginine amino acid residues along the total length of the polypeptide. Thus, the arginine-rich polypeptide can includes at least 10% arginine residues, at least 15% arginine residues, at least 20% arginine residues, at least 25% arginine residues, at least 30% arginine residues, at least 35% arginine residues, at least 40% arginine residues, at least 45% arginine residues, at least 50% arginine residues, at least 55% arginine residues, at least 60% arginine residues, at least 65% arginine residues, at least 70% arginine residues, at least 75% arginine residues, at least 80% arginine residues, at least 85% arginine residues, at least 90% arginine residues, or at least 95% arginine residues. In some embodiments, the arginine-rich polypeptide can include at least 45% arginine residues such as, for example, the polypeptide of SEQ ID NO:1. In other embodiments, the arginine-rich polypeptide can include at least 50% arginine residues such as, for example, the polypeptide of SEQ ID NO:2. In still other embodiments, the arginine-rich polypeptide can include at least 100% arginine residues such as, for example, the polypeptide of SEQ ID NO:5. In still other embodiments, the arginine-rich polypeptide can include protamine such as, for example, any one of SEQ ID NO:6-13, protamine from any other species, or a protein that is produced recombinantly or any by any other non-biological process that is structurally similar to a protamine.

As used herein, "structurally similar" refers to the degree of amino acid sequence identity between two polypeptides. For polypeptides, structural similarity is generally determined by aligning the residues of the two polypeptides (for example, a candidate polypeptide and a reference) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide (e.g., any one of SEQ ID NO:5-13). A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids and "similarity" refers to the presence of not only identical amino acids but also the presence of conservative substitutions. A conservative substitution for an amino acid in an arginine-rich polypeptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH$_2$. Likewise, biologically active analogs of a polypeptide containing deletions or additions of one or more contiguous or noncontiguous amino acids that do not eliminate a functional activity of the polypeptide are also contemplated.

An arginine-rich polypeptide, as described herein, includes polypeptides having at least 85% sequence similarity to the amino acid sequence of any suitable reference polypeptide. Suitable reference polypeptides include any one of SEQ ID NO:5-13 or the known amino acid sequence of protamine from any species of animal. Thus, an arginine-rich polypeptide can possess at least 85% sequence similarity, at least 86% sequence similarity, at least 87% sequence similarity, at least 88% sequence similarity, at least 89% sequence similarity, at least 90% sequence similarity, at least 91% sequence similarity, at least 92% sequence similarity, at least 93% sequence similarity, at least 94% sequence similarity, at least 95% sequence similarity, at least 96% sequence similarity, at least 97% sequence similarity, at least 98% sequence similarity, or at least 99% sequence similarity to a suitable reference polypeptide.

An arginine-rich polypeptide, as described herein, includes polypeptides having at least 85% sequence identity to the amino acid sequence of any suitable reference polypeptide. Suitable reference polypeptides include any one of SEQ ID NO:5-13 or the known amino acid sequence of protamine from any species of animal. Thus, an arginine-rich polypeptide can possess at least 85% sequence identity, at least 86% sequence identity, at least 87% sequence identity, at least 88% sequence identity, at least 89% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity to a suitable reference polypeptide.

The polypeptides of the present invention can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on nickel columns. Such gene modification techniques and suitable additional sequences are well known in the molecular biology arts.

The arginine content of a polypeptide may, alternatively, be expressed in terms of the percentage of non-arginine residues in the arginine-rich polypeptide. Thus, the arginine-rich polypeptide can include no more than 90% non-arginine amino acid residues such as, for example, no more than 85% non-arginine amino acid residues, no more than 80% non-arginine amino acid residues, no more than 75% non-arginine amino acid residues, no more than 70% non-arginine amino acid residues, no more than 65% non-arginine amino acid residues, no more than 60% non-arginine amino acid residues, no more than 55% non-arginine amino acid residues, no more than 50% non-arginine amino acid residues, no more than 45% non-arginine amino acid residues, no more than 40% non-arginine amino acid residues, no more than 35% non-arginine amino acid residues, no more than 30% non-arginine amino acid residues, no more than 25% non-arginine amino acid residues, no more than 20% non-arginine amino acid residues, no more than 15% non-arginine amino acid residues, no more than 10% non-arginine amino acid residues, no more than 5% non-arginine amino acid residues, no more than 4% non-arginine amino acid residues, no more than 3% non-arginine amino acid residues, no more than 2% non-arginine amino acid residues, or no more than 1% non-arginine amino acid residues. In some embodiments, the arginine-rich polypeptide can include no more than 55% non-arginine residues such as, for example, the polypeptide of SEQ ID NO:1. In other embodiments, the arginine-rich polypeptide can include no more than 50% non-arginine residues such as, for example, the polypeptide of SEQ ID NO:2. In still other embodiments, the arginine-rich polypeptide can include no non-arginine residues such as, for example, the polypeptide of SEQ ID NO:5.

The arginine-rich polypeptide also can include a minimum total length of at least 15 amino acid residues such as, for example, at least 16 amino acid residues, at least 17 amino acid residues, at least 18 amino acid residues, at least 19 amino acid residues, at least 20 amino acid residues, at least 25 amino acid residues, at least 30 amino acid residues, at least 50 amino acid residues, at least 55 amino acid residues, at least 60 amino acid residues, at least 65 amino acid residues, at least 70 amino acid residues, at least 75 amino acid residues, at least 80 amino acid residues, at least 85 amino acid residues, at least 90 amino acid residues, at least 95 amino acid residues, or at least 100 amino acid residues. In some embodiments, the arginine-rich polypeptide can include at least 18 amino acid residues such as, for example, the polypeptide of SEQ ID NO:2. In other embodiments, the arginine-rich polypeptide can include at least 20 amino acid residues such as, for example, the polypeptide of SEQ ID NO:1. In still other embodiments, the arginine-rich polypeptide can include at least 28 amino acid residues such as, for example, the polypeptide of SEQ ID NO:5.

Thus, in some embodiments, the arginine-rich polypeptide can include a minimum number of arginine amino acid residues such as, for example, a minimum of at least nine arginine residues, at least ten arginine residues, at least 11 arginine residues, at least 12 arginine residues, at least 13 arginine residues, at least 14 arginine residues, at least 15 arginine residues, at least 16 arginine residues, at least 17 arginine residues, at least 18 arginine residues, at least 19 arginine residues, at least 20 arginine residues, at least 25 arginine residues, at least 30 arginine residues, at least 50 arginine residues, at least 55 arginine residues, at least 60 arginine residues, at least 65 arginine residues, at least 70 arginine residues, at least 75 arginine residues, at least 80 arginine residues, at least 85 arginine residues, at least 90 arginine residues, at least 95 arginine residues, or at least 100 arginine residues.

The arginine-rich polypeptide may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the arginine-rich polypeptide, its use in the therapeutic compositions is contemplated. Supplementary active ingredients also can be incorporated into the composition. As used herein, "pharmaceutically acceptable" refers to a material that is not biologically or otherwise undesirable, i.e., the material may be administered to an individual along with the arginine-rich polypeptide without causing any undesirable biological effects or interacting in a deleterious manner with any of the other components of the pharmaceutical composition in which it is contained.

The arginine-rich polypeptide may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the vaginal mucosa. A composition also can be administered via a sustained or delayed release.

Thus, the arginine-rich polypeptide may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the arginine-rich polypeptide into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of arginine-rich polypeptide administered can vary depending on various factors including, but not limited to, the specific arginine-rich polypeptide being administered, the weight, physical condition, and/or age of the subject, whether the treatment is prophylactic or therapeutic, and/or the route of administration. Thus, the absolute weight of arginine-rich polypeptide included in a given unit dosage form can vary widely, and depends upon factors such as the species, age, weight and physical condition of the subject, and/or the method of administration. Accordingly, it is not practical to set forth generally the amount that constitutes an amount of the arginine-rich polypeptide effective for all possible applications. Those of ordinary skill in the art, however, can readily determine the appropriate amount with due consideration of such factors.

Thus, this disclosure further describes methods of treating an infection. Generally, the method includes administering or applying the composition to a subject. As used herein, the term "treat" or variations thereof refer to reducing, limiting progression, ameliorating, or resolving, to any extent, the symptoms or signs related to a condition. As used herein, "symptom" refers to any subjective evidence of disease or of a patient's condition, while "sign" or "clinical sign" refers to an objective physical finding relating to a particular condition capable of being found by one other than the patient.

A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject. Treatment that is prophylactic—e.g., initiated before a subject manifests a symptom or clinical sign of the condition such as, for example, while an infection remains subclinical—is referred to herein as treatment of a subject that is "at risk" of having the condition. As used herein, the term "at risk" refers to a subject that may or may not actually possess the described risk. Thus, for example, a subject "at risk" of infectious condition is a subject present in an area where other individuals have been identified as having the infectious condition and/or is likely to be exposed to the infectious agent even if the subject has not yet manifested any detectable indication of infection by the microbe and regardless of whether the subject may harbor a subclinical amount of the microbe. As another example, a subject "at risk" of a non-infectious condition is a subject possessing one or more risk factors associated with the condition such as, for example, genetic predisposition, ancestry, age, sex, geographical location, lifestyle, or medical history.

Accordingly, the composition can be administered before, during, or after the subject first exhibits a symptom or clinical sign of the condition or, in the case of infectious conditions, before, during, or after the subject first comes in contact with the infectious agent. Treatment initiated before the subject first exhibits a symptom or clinical sign associated with the condition may result in decreasing the likelihood that the subject experiences clinical evidence of the condition compared to an animal to which the composition is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to an animal to which the composition is not administered, and/or completely resolving the condition.

For example, certain arginine-rich polypeptides may be administered at the same dose and frequency for which the compound has received regulatory approval. In other cases, certain arginine-rich polypeptides may be administered at the same dose and frequency at which the drug is being evaluated in clinical or preclinical studies. One can alter the dosages and/or frequency as needed to achieve a desired level of the arginine-rich polypeptide. Thus, one can use standard/known dosing regimens and/or customize dosing as needed.

In some embodiments, the method can include administering sufficient arginine-rich polypeptide to provide a dose of, for example, from about 100 ng/kg to about 50 mg/kg to the subject, although in some embodiments the methods may be performed by administering arginine-rich polypeptide in a dose outside this range. In some of these embodiments, the method includes administering sufficient arginine-rich polypeptide to provide a dose of from about 10 µg/kg to about 5 mg/kg to the subject, for example, a dose of from about 100 µg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$=(wt $kg^{0.425}$×height $cm^{0.725}$)×0.007184.

In some embodiments, the method can include administering sufficient arginine-rich polypeptide to provide a dose of, for example, from about 0.01 $mg/m^2$ to about 10 $mg/m^2$.

Accordingly, a pharmaceutical composition can include an arginine-rich polypeptide (e.g., PrS) provided at a concentration suitable to provide the desired dosage. For example, the arginine-rich polypeptide (e.g., PrS) can be provided at a minimum concentration of at least 1 µM such as, for example, at least 2 at least 5 at least 10 or at least 20 µM. In particular embodiments, the arginine-rich polypeptide is PRS, provided at a concentration of 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, or 20 µM.

In some embodiments, the arginine-rich polypeptide may be administered, for example, from a single dose to multiple doses, although in some embodiments the method can be performed by administering the arginine-rich polypeptide at a frequency outside this range. In certain embodiments, the arginine-rich polypeptide may be administered from a single dose to once per month, to multiple times per day such as, for example, once per week, three times per week, once per day, three times per day, or six times per day.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

In the preceding description, it is to be understood that the particular examples, materials, amounts, and procedures are to be interpreted broadly in accordance with the scope and spirit of the invention as set forth herein.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

---

Sequence Listing Free Text

SEQ ID NO: 1-gp19 ds-tat (AnaSpec #63818; AnSpec, Inc., Fremont, CA)
YGRKKRRQRRRCSTRIRRQL
          10          20

SEQ ID NO: 2-Gp19 dstat scramble (AnaSpec #63855; AnSpec, Inc., Fremont, CA)
RKKRRQRRRCLRITRQSR
          10

SEQ ID NO: 3-R9 (AnaSpec #61204; AnSpec, Inc., Fremont, CA)
RRRRRRRRR

SEQ ID NO: 4-TAT (AnaSpec #60023-1; AnSpec, Inc., Fremont CA)
YGRKKRRQRRR
          10

SEQ ID NO: 5-PolyR (Sigma P4663; Sigma-Aldrich. St. Louis, MO)
RRRRRRRRRRRRRRRRRRRRRRRRRRR ($R_{1-59}$)
          10          20

SEQ ID NO: 6-Human sperm protamine P1
MARYRCCRSQSRSRYYRQRQRSRRRRRSCQTRRRAMRCCRPRYRPRCRRH
          10          20          30          40          50

SEQ ID NO: 7-Human sperm protamine P2, isoform 1
MVRYRVRSLSERSHEVYRQQLHGQEQGHHGQEEQGLSPEHVEVYERTHGQSHYRRRHCSRRRLHRIHRRQHRSCRR
          10          20          30          40          50          60          70
RKRRSCRHRRRHRRGCRTRKRTCRRH
     80          90          100

SEQ ID NO: 8-*Scylliorhinus caniculus* protamine Z3
ARSRSRRSYGRGRRRGGRRRRRRRRRRRGGR
          10          20          30

SEQ ID NO: 9-*Oncorhynchus keta* (Chum salmon) (*Salmo keta*) protamine
MPRRRRSSSRPVRRRRRPRVSRRRRRRGGRRRR
          10          20          30

SEQ ID NO: 10-*Bos taurus* protamine P1
ARYRCCLTHSGSRCRRRRRRRCRRRRRRFGRRRRRRVCCRRYTVIRCTRQ
          10          20          30          40          50

SEQ ID NO: 11-*Oncorhynchus mykiss* (Rainbow trout) (*Salmo gairdneri*) protmamine-1B
PRRRRRSSSRPIRRRRPRRVSRRRRRGGRRRR
          10          20          30

SEQ ID NO: 12-*Oncorhynchus mykiss* (Rainbow trout) (*Salmo gairdneri*) protmamine-2B
MPRRRRSSSRPVRRRRRPRVSRRRRRRGGRRRR
          10          20          30

Sequence Listing Free Text

SEQ ID NO: 13-*Oncorhynchus mykiss* (Rainbow trout) (*Salmo gairdneri*) protmamine-PTP4
MPRRRRASRRIRRRRRPRVSRRRRGGRRRRR
          10         20        30

What is claimed is:

1. A composition comprising:
   a complex consisting of:
      hyaluronic acid; and
      an arginine-rich polypeptide comprising at least nine arginine amino acid residues, wherein the at least nine arginine amino acid residues are at least 10% of the polypeptide amino acid residues; and
   a pharmaceutically acceptable carrier;
   wherein the composition inhibits binding of human papilloma virus (HPV) to a cell surface.

2. The composition of claim 1, wherein the arginine-rich polypeptide comprises protamine.

3. The composition of claim 2 wherein the protamine is in the form of protamine sulfate (PrS).

4. The composition of claim 1, wherein the concentration of arginine-rich polypeptide is at least 1 µM.

5. The composition of claim 1, wherein the composition is a topical formulation.

6. The composition of claim 1, wherein the composition further comprises a vaginal moisturizer composition.

7. A method of inhibiting a human papilloma virus (HPV) from binding to a cell, the method comprising:
   contacting the cell prior to HPV infection with an amount of a composition effective to inhibit HPV binding to the cell, the composition comprising:
      a complex comprising:
         hyaluronic acid; and
         an arginine-rich polypeptide comprising at least nine arginine amino acid residues, wherein the at least nine arginine amino acid residues are at least 10% of the polypeptide amino acid residues; and
      a pharmaceutically acceptable carrier.

8. The method of claim 7, wherein the arginine-rich polypeptide comprises protamine.

9. The method of claim 8, wherein the protamine is in the form of protamine sulfate (PrS).

10. The method of claim 7, wherein the arginine-rich polypeptide is provided in a concentration of at least 1 µM.

11. The method of claim 7, wherein the composition is formulated for topical administration.

12. A method of inhibiting intracellular processing of human papilloma virus (HPV) by a cell after HPV attaches to the cell, the method comprising:
   contacting the cell with an amount of a composition effective to inhibit intracellular processing of HPV by the cell, the composition comprising:
      a complex comprising:
         hyaluronic acid; and
         an arginine-rich polypeptide comprising at least nine arginine amino acid residues, wherein the at least nine arginine amino acid residues are at least 10% of the polypeptide amino acid residues; and
      a pharmaceutically acceptable carrier.

13. The method of claim 12, wherein the arginine-rich polypeptide comprises protamine.

14. The method of claim 13, wherein the protamine is in the form of protamine sulfate (PrS).

15. The method of claim 12, wherein the arginine-rich polypeptide is provided in a concentration of at least 1 µM.

16. The method of claim 12, wherein the composition is formulated for topical administration.

17. A method of treating a subject having, or at risk of having, a human papilloma virus (HPV) infection, the method comprising:
   administering to the subject an amount of a composition effective to inhibit infection by HPV, the composition comprising:
      a complex comprising:
         hyaluronic acid; and
         an arginine-rich polypeptide comprising at least nine arginine amino acid residues, wherein the at least nine arginine amino acid residues are at least 10% of the polypeptide amino acid residues; and
      a pharmaceutically acceptable carrier.

18. The method of claim 17, wherein the composition inhibits infection of cells by human papilloma virus (HPV).

19. The method of claim 18, wherein the composition inhibits binding of HPV to the cells.

20. The method of claim 17, wherein the arginine-rich polypeptide comprises protamine.

21. The method of claim 20, wherein the protamine is in the form of protamine sulfate (PrS).

22. The method of claim 17, wherein the arginine-rich polypeptide is provided in a concentration of at least 1 µM.

23. The method of claim 17, wherein the composition is formulated for topical administration.

* * * * *